US012765835B2

(12) United States Patent
Wang et al.

(10) Patent No.: US 12,765,835 B2
(45) Date of Patent: Oct. 20, 2026

(54) MINIMALLY INVASIVE CONTINUOUS ANALYTE MONITORING FOR CLOSED-LOOP TREATMENT APPLICATIONS

(71) Applicant: The Regents of the University of California, Oakland, CA (US)

(72) Inventors: Joseph Wang, San Diego, CA (US); Irene Litvan, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1206 days.

(21) Appl. No.: 17/597,732

(22) PCT Filed: Jul. 23, 2020

(86) PCT No.: PCT/US2020/043295
§ 371 (c)(1),
(2) Date: Jan. 20, 2022

(87) PCT Pub. No.: WO2021/016465
PCT Pub. Date: Jan. 28, 2021

(65) Prior Publication Data

US 2022/0257181 A1 Aug. 18, 2022

Related U.S. Application Data

(60) Provisional application No. 62/877,826, filed on Jul. 23, 2019.

(51) Int. Cl.
*A61B 5/00* (2006.01)
*A61B 5/145* (2006.01)
(Continued)

(52) U.S. Cl.
CPC ........ *A61B 5/4839* (2013.01); *A61B 5/14514* (2013.01); *A61B 5/14532* (2013.01);
(Continued)

(58) Field of Classification Search
CPC .. A61B 5/1451–14514; A61B 5/14532; A61B 5/14546; A61B 5/1473–14735;
(Continued)

(56) References Cited

U.S. PATENT DOCUMENTS

| | | | | |
|---|---|---|---|---|
| 9,737,247 B2 | 8/2017 | Wang et al. | | |
| 2008/0200789 A1 * | 8/2008 | Brister | ................. | A61B 5/6849 600/347 |

(Continued)

FOREIGN PATENT DOCUMENTS

| | | | |
|---|---|---|---|
| WO | WO-2017181027 A1 * | 10/2017 | ........ A61M 37/0015 |

OTHER PUBLICATIONS

Arroyo-Curras, N. et al. "Real-time measurement of small molecules directly in awake, ambulatory animals" PNAS, 2017, vol. 114, No. 4, pp. 645-650.

(Continued)

*Primary Examiner* — Tse Chen
(74) *Attorney, Agent, or Firm* — Ashurst Perkins Coie US LLP

(57) ABSTRACT

Disclosed are devices, systems and methods for minimally-invasive and continuous analyte monitoring for closed-loop applications, such as drug delivery. In some aspects, a multi-modal microneedle sensing platform for continuous minimally-invasive orthogonal electrochemical monitoring of levodopa (L-Dopa) is disclosed, which uses parallel simultaneous independent enzymatic-amperometric and non-enzymatic voltammetric detection of L-Dopa using different microneedles on the same sensor array patch.

17 Claims, 18 Drawing Sheets

(51) Int. Cl.
*A61B 5/1473* (2006.01)
*A61B 5/1486* (2006.01)
*G01N 33/68* (2006.01)

(52) U.S. Cl.
CPC ........ *A61B 5/14546* (2013.01); *A61B 5/1473* (2013.01); *A61B 5/14865* (2013.01); *A61B 5/685* (2013.01); *G01N 33/6812* (2013.01); *A61B 2560/0223* (2013.01); *A61B 2562/164* (2013.01); *G01N 2610/00* (2013.01)

(58) Field of Classification Search
CPC .... A61B 5/1477; A61B 5/1486–14865; A61B 5/4839; A61B 5/685; A61B 2562/164
See application file for complete search history.

(56) References Cited

U.S. PATENT DOCUMENTS

| | | | | |
|---|---|---|---|---|
| 2009/0131778 | A1 | 5/2009 | Jina et al. | |
| 2010/0292557 | A1* | 11/2010 | Pesach | A61B 5/1491 607/113 |
| 2017/0226557 | A1* | 8/2017 | Wang | C12Q 1/26 |
| 2018/0136191 | A1* | 5/2018 | Asvadi | A61B 5/4266 |
| 2019/0009019 | A1* | 1/2019 | Shor | A61M 5/31528 |
| 2019/0076075 | A1* | 3/2019 | Miller | A61B 5/150022 |
| 2019/0125223 | A1 | 5/2019 | Wang et al. | |
| 2019/0223795 | A1* | 7/2019 | Patolsky | A61B 5/14865 |
| 2020/0158678 | A1* | 5/2020 | Kawde | G01N 27/48 |
| 2020/0274135 | A1* | 8/2020 | Ehsan | G01N 33/00 |

OTHER PUBLICATIONS

ISA, International Search Report and Written Opinion for International Application No. PCT/US2020/043295. Mail Date: Oct. 16, 2020. 11 pages.
Mohan, A. et al. “Continuous minimally-invasive alcohol monitoring using microneedle sensor arrays” Biosens. Bioelectron.; 2017, vol. 91, pp. 574-579.
O’Mahony, A. et al. “Orthogonal Detection of Nitroaromatic Explosives via Direct Voltammetry Coupled to Enzyme-Mediated Biocatalysis” Electroanalysis, 2012, vol. 24, No. 9, pp. 1811-1816.
Sharma, S. et al. “A pilot study in humans of microneedle sensor arrays for continuous glucose monitoring” Cronfa, 2018. 23 pages.

* cited by examiner

MINIMALLY INVASIVE CONTINUOUS ANALYTE MONITORING FOR CLOSED-LOOP TREATMENT APPLICATIONS

This patent document is a U.S.C. § 371 National Stage application of International Application No. PCT/US2020/043295 entitled "MINIMALLY INVASIVE CONTINUOUS ANALYTE MONITORING FOR CLOSED-LOOP TREATMENT APPLICATIONS" filed on Jul. 23, 2020 which further claims priority to and benefits of U.S. Provisional Patent Application No. 62/877,826 entitled "MINIMALLY INVASIVE CONTINUOUS ANALYTE MONITORING FOR CLOSED-LOOP TREATMENT APPLICATIONS" filed on Jul. 23, 2019. The entire contents of the aforementioned patent applications are incorporated by reference as part of the disclosure of this patent document.

TECHNICAL FIELD

This patent document relates to analyte monitoring devices and techniques.

BACKGROUND

Biosensors can provide real-time detection of physiological substances and processes in living things. A biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents, which can be useful for various health care applications, including researching, diagnosing and treating diseases.

Parkinson disease (PD) is the second most common neurodegenerative disorder after Alzheimer's disease. PD leads to disability, affects patients' and families' quality life and finances and increases health care cost. An estimated 7 to 10 million people worldwide have PD, including over one million Americans, with sixty thousand Americans being diagnosed every year.

Levodopa (L-Dopa) is the most effective medication for treating PD. However, because dose optimization is currently based on patients' report of symptoms, which are difficult for patients to describe, the management of PD is challenging.

SUMMARY

Disclosed are devices, systems and methods for minimally-invasive and continuous analyte monitoring for closed-loop treatment applications, such as drug delivery.

In some aspects, the disclosed technology provides a microneedle-based sensor platform for accurately detecting a concentration of an analyte (e.g., a drug) using parallel, multi-modal detection techniques at separate microneedle tips to greatly enhance the detection reliability.

In some embodiments, for example, a minimally-invasive and continuous analyte monitoring system includes an electrochemical/biocatalytic microneedle sensor array operable for continuous monitoring of a target analyte in a biological fluid, such as L-Dopa, glucose, or other analyte in interstitial fluid (ISF) or whole blood sample. In an example embodiment, a multi-modal microneedle sensing platform includes different microneedle electrodes arranged in an array on a wearable patch, where the array uses parallel, simultaneous, and independent detection techniques (e.g., enzymatic-amperometric and non-enzymatic voltammetric interrogation) of the same target analyte (e.g., L-Dopa). For critical monitoring of L-Dopa, for example, such real-time parallel, simultaneous, and independent L-Dopa sensing offers a built-in redundancy—based on separate recognition routes and detection principles—and greatly enhances the information content of the microneedle L-Dopa sensor arrays. In some example implementations, this can be accomplished by rapid detection of L-Dopa using square-wave voltammetry (SWV) and chronoamperometry at unmodified and tyrosinase-modified carbon-paste microneedle electrodes, respectively.

Example implementations of various embodiments of a minimally-invasive and continuous analyte monitoring system, described herein, demonstrate ex-vivo L-Dopa detection capability. It is envisioned that the disclosed continuous L-Dopa monitoring capability would constitute a paradigm shift by allowing Parkinson disease patients and physicians to better manage the disease and could, as with a closed-loop glucose monitor-insulin pump system, lead to the development of a metered L-Dopa pump that ensures accurate L-Dopa administration.

Also, in some aspects, the disclosed technology provides a microneedle sensor array of a minimally-invasive and continuous analyte monitoring system interfaced with a closed-loop feedback sensor-delivery system that uses the estimated drug-analyte level (e.g., L-Dopa concentration level in blood) as a feedback signal for adjusting the dose of the drug-analyte (e.g., L-Dopa) through subcutaneous delivery. In some embodiments, for example, L-Dopa reservoirs on the microneedle sensor array itself (e.g., adjacent to the microneedle sensors) can also be used in connection to such closed-loop operation. Yet, in some embodiments, for example, an L-Dopa micropump can be integrated with the microneedle patch.

The subject matter described in this patent document can be implemented in specific ways that provide one or more of the following features.

DETAILED DESCRIPTION

Figure 1A:
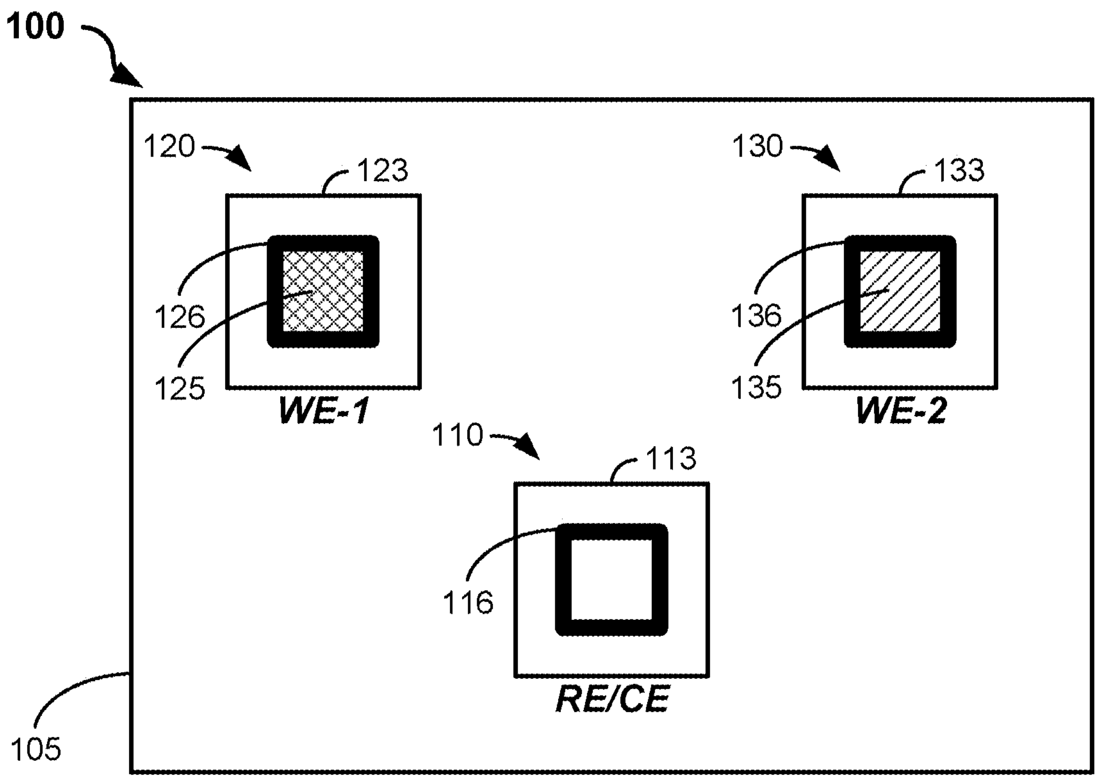
FIG. 1A shows a block diagram depicting an electrochemical microneedle sensor device having at least two microneedle-based working electrodes for parallel, simultaneous, and orthogonal sensing of a single analyte in accordance with the present technology.

For analyte monitoring and drug delivery applications that are based on determining dosage and/or timing of a drug administration using sensing of a concentration of a target compound in one or several fluids and/or tissues of a human body, the ability to determine the concentration of that target compound in real time and with utmost accuracy is paramount. Example drug delivery applications of this kind include insulin injection based on glucose sensing in the blood or in the interstitial fluid (ISF) of a human body. Another potential application of the same kind is L-Dopa administration based on L-Dopa levels measured in the blood or in the ISF for management of the Parkinson disease.

Electrochemical sensors, including wearable ones, are an attractive choice for measurement of the target compound concentration in body fluids. However, traditional utilization of a single sensing modality and/or type of an electrochemical sensor used for such purposes leaves a significant gap for needed improvements of the sensor specificity, sensitivity, limit of detection, as well as other important analytic parameters of the sensor. For in vivo biomedical applications, such as diabetes and Parkinson disease, sensors with a single-sensing modality fail to provide the necessary redundancies and checks to ensure the critical accuracy needed to make drug treatment decisions. For example, existing sensor technologies with built-in redundancies merely expand the number of sensors, but fail to provide checks on detection accuracies that can inform on and prevent system failures that may be present within the sensing modality. As such, existing single-mode sensor array devices, no matter how many redundant sensors on the array, may inaccurately measure concentration or other parameters of a target analyte for a variety of reasons, including the presence of interfering species in the medium of the target analyte, environmental effects, or systemic causes. Yet, implementing multi-modal sensing has, to date, been restricted due to constraints on sensor device configuration and equipment requirements, among other challenges. As such, a single, portable, wearable, minimally-invasive electrochemical sensor platform directed to simultaneously measuring a single analyte using multiple sensing techniques has not yet been successfully realized for widespread use for clinically-relevant (accurate) in vivo analyte sensing applications. Therefore, it would be beneficial to provide a multi-modal detection system on a single platform (e.g., wearable patch) for enhancing detection reliability in in vivo biomedical sensing and treatment applications, particularly for disease monitoring and treatment in a closed-loop system.

The disclosed technology provides a microneedle-based sensor array platform for accurately detecting a concentration of an analyte (e.g., a drug) using parallel, multi-modal detection techniques at separate microneedle tips to greatly enhance the detection reliability. The disclosed devices, systems, and methods are designed to address the shortcomings of conventional approaches and close that gap by simultaneous use of independent measurement schemes, based on two or more distinct analyte detection processes, which can dramatically increase the information content of the data collected and offers substantially improved reliability of the target analyte detection compared to the existing technology. In particular, the simultaneous use of independent electrochemical measurement techniques, based on at least two distinct detection modes of the microneedle electrode sensor, dramatically increases the information content about the monitored analyte and offers substantially improved reliability, while minimizing the occurrence of false alarms. The disclosed technology also provides a microneedle-based sensor array interfaced with a closed-loop feedback drug-delivery system that uses the estimated drug-analyte level detected by the sensor contingent as a feedback for controlling the timing and dose of the drug-analyte through subcutaneous delivery.

Although the importance of real-time monitoring of a target analyte in body fluids (e.g., blood or ISF) for real-time adjustments of a drug dose and timing of the drug administration is discussed below with respect to the Parkinson disease and the drug L-Dopa, the disclosed technology is not limited to any particular disease or target analyte.

Parkinson Disease

Parkinson disease (PD) is a pervasive neurodegenerative disease affecting over 6 million individuals worldwide. Manifestations of PD typically appear in those older than 60, with progressive motor symptoms characterized by slowness, rigidity, and tremor, eventually advancing to gait disturbances. In addition to motor symptoms, PD patients exhibit non-motor manifestations, including mood, cognitive, and autonomic disturbances. Non-motor symptoms also fluctuate and, combined with motor fluctuations, lead to significant disability and high healthcare cost. The combined direct and indirect cost of PD is estimated to exceed $14 billion annually in the United States alone. These deficits are related to a loss of dopaminergic neurons in the substantia nigra and can be improved with L-Dopa replacement.

L-Dopa is naturally synthesized in the nervous system from the amino acid L-tyrosine and serves as the precursor to the catecholamine neurotransmitters dopamine, norepinephrine, and epinephrine. L-Dopa traverses the protective blood-brain barrier by active amino acid transport, whereas the other catecholamines cannot traverse. Within the brain, L-Dopa is decarboxylated to dopamine. Thus, oral L-Dopa supplements are widely used to increase dopamine concentrations to treat symptoms of PD.

At early stages, PD patients benefit significantly from L-Dopa therapy without complications. However, with disease progression, increasing dopamine neuronal loss in conjunction with L-dopa's short half-life causes symptomatic fluctuations. To maintain the same therapeutic effect, L-Dopa doses must be gradually increased and administered at increasingly shorter time intervals that may be as frequent as every hour. Over time, the threshold for side-effects decreases, and patients are more likely to experience wearing-off of L-dopa between doses, resulting in a narrowing therapeutic window for a given dose. During the course of treating PD, patients can also experience different complications in response to L-Dopa, which can also eventually lead to a narrowing window of therapeutic efficacy for a given L-Dopa dose.

In addition to the debilitating effects and complexities in treating PD, the financial cost of treating PD patients is extremely high. For example, the combined direct and indirect cost of PD is estimated to exceed $14 billion annually in the United States alone. To manage fluctuating symptoms, PD patients must return to healthcare providers frequently to adjust the dosing for adequate symptom control. This process is a burden to both PD patients (and their caregivers) and the healthcare professionals (e.g., physicians and healthcare systems) treating the patients. Furthermore, and surprisingly, these frequent evaluations of PD patients are performed on the basis of the patients' testimony about frequency and severity of motor symptoms and dyskinesias, and the healthcare providers' visual assessment of fine motor control. Healthcare professionals rely on patients to report the symptoms, but most patients have difficulty distinguishing between dyskinesias or tremors and/or the time of their antiparkinsonian medication intake.

Selection of appropriate L-Dopa dosing is highly personalized, and the timing and quantity of doses must be adjusted based on control of symptoms, which can vary from hour to hour. Therefore, there is an urgent need to improve adjustments of individual doses of the drug given the variable responses of motor and non-motor symptoms to L-Dopa. Improvements in the drug dose adjustments would, in turn, significantly improve the management of PD symptoms.

Accordingly, a reliable and accurate wearable sensor device that continuously measures L-Dopa in real time is urgently needed to provide individualized, timely feedback on a proper L-Dopa dosing regimen in a decentralized and rapid fashion. Measuring L-Dopa levels in real time will enable PD patients and physicians to take proactive measures to optimize the therapeutic dopaminergic regimen, reducing the likelihood of hospital admissions due to complications such as severe dyskinesias, freezing, and gait disturbances leading to falls and injury. Moreover, since continuously infused and properly dosed L-Dopa can prevent dyskinesias and lead to reduced fluctuations and disability, more invasive treatment such as deep brain stimulation surgery, could be delayed.

To maintain the same therapeutic effect, L-Dopa doses must be adjusted to avoid the consequences of low doses leading to symptoms, such as parkinsonism, anxiety and depression or higher concentrations that result in dyskinesias, psychosis, orthostatic hypotension, etc. Considering that the minimal L-Dopa dose necessary to produce an observable antiparkinsonian effect remains the same for stable and fluctuating patients, but the threshold dose for dyskinesias significantly lowers in more affected groups, it seems relevant to always treat patients with the lowest possible dose. This knowledge is critical for better PD management, particularly at moderate to advanced stages.

Non-invasive real-time measurement of PD patients' L-Dopa concentrations in biofluids using a wearable sensor would not only allow better management of middle and late PD stages but can also improve the management of PD at early stages. Because administration of high doses of L-Dopa at early PD stages leads to earlier development of PD fluctuations, knowledge of L-Dopa concentrations will allow the use of lower L-Dopa dose at early stages which will likely delay the onset of fluctuations.

Presently, plasma levels of L-dopa are commonly measured using high-performance liquid chromatography (HPLC) and correlate accurately with motor symptoms' severity. However, HPLC is not a viable method for timely adjustment of L-Dopa dosage because of its slow delivery of the results and high costs. Yet, electrochemical techniques could be used for in-vitro measurements of L-Dopa, e.g., by use of electrodes modified with variety of nanoscale materials towards accelerating the L-Dopa oxidation process.

Wearable sensor technology for Parkinson disease monitoring applications has advanced rapidly in recent years to provide tremendous opportunities for improving personalized healthcare, such as monitoring motor fluctuations of PD patients and the severity of Parkinsonian symptoms. However, there exists a need for the development of viable wearable chemical sensors for accurately monitoring these patients towards improved management of PD—particularly, for example, through L-Dopa dose adjustments based on continuous real-time monitoring of L-Dopa in Parkinson's patient blood or other physiologically-relevant fluids. There is an immense need and promise for developing a wearable electrochemical sensing platform for continuous monitoring of L-Dopa in Parkinson's patient blood or other physiologically-relevant fluids.

Disclosed are devices, systems, and methods for minimally-invasive, simultaneous multi-modal, and continuous analyte monitoring in the blood and/or other fluid and/or tissue of a living organism for closed-loop applications, such as drug delivery. The disclosed minimally-invasive, simultaneous multi-modal, and continuous analyte monitoring and closed-loop drug delivery platform utilizes microneedle arrays on a wearable sensing and chemical delivery platform, which enables rapid, continuous, painless, and minimally-invasive transdermal sensing of various biomarkers in the body interstitial fluid (ISF), and in some implementations, subcutaneous drug delivery in a closed-loop configuration with the sensing microneedle contingent.

In some embodiments in accordance with the disclosed technology, a dual-sensing electrochemical/biocatalytic microneedle sensor array is described for continuous minimally-invasive monitoring of L-Dopa. This dual-sensing platform can provide rich electrochemical information towards measurements of the target L-Dopa analyte compared to common single modality sensing routes. In some embodiments, the dual-sensing electrochemical/biocatalytic microneedle sensor array device includes two-working electrode microneedle array constructed by packing hollow microneedles with different carbon paste (CP) electrode transducer. Whereas, in some embodiments, for example, the modified electrodes can include carbon nanotubes (CNT)-chitosan-glassy carbon electrode (GCE), CNT-chitosan-screen printed electrode (SPCE), CNT-gold nanoparticles-graphite electrode, SWCNT-GCE, GCE-MWCNT-polypyrrole, GCE-MWCNT-nickel hydroxide nanoparticles (NPs), 3D graphene foam, $TiO_2$ nanofiber-graphene oxide and nickel hexacyanoferrate-Au NPs-graphite.

These and other example features of the disclosed microneedle sensor array in accordance with the present technology are described below.

FIG. 1A shows a block diagram depicting an example embodiment of an electrochemical microneedle sensor device 100 having at least two microneedle-based working electrodes for parallel, simultaneous, and orthogonal sensing of a single analyte in accordance with the present technology, in which the at least two microneedle-based working electrodes are disposed on a substrate proximate a reference and/or counter microneedle-based electrode. As shown in the diagram, the device 100 can include a first microneedle electrode 110 configured as a reference electrode, RE, and/or counter electrode, CE, for electrochemical sensing of the analyte, disposed on substrate 105. The device 100 can include a second microneedle electrode 120 configured as a first working electrode, WE-1, and a third microneedle electrode 130 configured as a second working electrode, WE-2, each disposed on the substrate 105. The microneedle electrodes 110, 120, and 130 of the electrochemical microneedle sensor device 100 include a microneedle structure and an electrode probe structure. The microneedle structure includes an exterior wall spanning outward from a base surface (e.g., located at the substrate 105 surface) and forming an apex at a terminus point of the exterior wall, where, at a portion of the exterior wall is an opening leading in to a hollow interior (or cavity) of the needle structure defined by an interior wall. In some embodiments, the microneedle structure can have a pyramidal geometry (e.g., trigonal pyramidal with three exterior walls or square pyramidal with four exterior walls); whereas in some embodiments, the microneedle structure can have a conical geometry.

The diagram of FIG. 1A shows microneedle structures 113, 123, and 133 of the microneedle electrodes 110, 120, and 130, respectively. In various example embodiments, the electrode probe structure is disposed within the interior or cavity of the respective microneedle structure. The diagram of FIG. 1A shows electrode probe structures 116, 126, and 136 of the microneedle electrodes 110, 120, and 130, respectively. For example, the electrode probe structure of an electrode of the microneedle sensor device 100 can include a silver (Ag), gold (Au) or platinum (Pt) wire and/or carbon paste (CP).

The substrate 105 used in example embodiments of the electrochemical microneedle sensor device 100 can include an electrically insulative material, such as a plastic material (e.g., polyethylene terephthalate (PET), polyethylene terephthalate glycol (PETG), polyethylene naphthalate (PEN), polyimide (PI), or other). The substrate 105 can be flexible and/or bendable and/or stretchable; and/or the substrate 105 can include an adhesive on at least one side of the substrate 105 to enable secure attachment of the device 100 to the subject, e.g., to skin.

In some implementations, the height of the microneedle structures (e.g., base to apex) can be in a range of 1 mm to 2 mm, e.g., preferably about 1500 μm. In some implementations, the diameter or width of the microneedle structure can be between 200 μm and 500 μm. The microneedle structures can be spaced at various spacings and arrangements, which can be selected based on the application of the microneedle sensor device 100. In some implementations, the microneedle structures are spaced apart in the tens of microns or hundreds of microns, base-to-base; for example, in some implementations, the microneedle structures are spaced about 1 mm apart from apex-to-apex. In some implementations, the microneedle structures are arranged on the substrate 105 in a linear array; whereas in some implementations the microneedle structures are arranged on the substrate 105 in a circular array, a rectangular array, a triangular array, or other patterned or non-patterned arrangement.

The microneedle structures and electrodes can be configured in other arrangements, e.g., as described in U.S. Pat. No. 9,737,247 is incorporated herein by reference in its entirety as part of the disclosure of this patent document.

In some embodiments, for example, depending on the electrochemical sensing technique to apply at the particular working electrode, the second microneedle electrode 120 and the third microneedle electrode 130 can include one or more functionalization materials. In FIG. 1A, the second microneedle electrode 120 includes a functionalization material 125 disposed on or integrated with at least a portion of the electrode probe structure 126 and/or within the opening or cavity of the microneedle structure 123. Similarly, in some embodiments, the third microneedle electrode 130 includes a functionalization material 135 disposed on or integrated with at least a portion of the electrode probe structure 136 and/or within the opening or cavity of the microneedle structure 133.

For example, in some embodiments, the electrochemical microneedle sensor device 100 is configured on a patch, which is attachable and conformable on a user's skin for mobile, remote monitoring applications. The patch can integrate the sensor, electronics, and/or actuator contingents of a sensor and/or drug-delivery device on a single substrate or single transferrable platform. In this disclosure, various embodiments of the electrochemical microneedle sensor device 100 is also referred to herein as the "sensor patch."

For example, in some embodiments, electrode probe structures of the microneedle electrodes 110, 120, and 130 can be of the same or differing materials, e.g. for varying detection purposes. For example, the electrode probe structure 126 can be a metal (e.g., gold) wire at least partially covered by a graphene film 125 functionalization material, while the electrode probe structure 136 can be functionalized with a biocatalyst 135 such as an enzyme, e.g., tyrosinase, glucose oxidase (GOx), or other, that, for example, can be attached to the electrode 130 via electropolymeric entrapment. In such embodiments, for example, enzyme-based detection of a target analyte, e.g. L-Dopa, can be performed using the functionalized microelectrode electrode 130 and non-enzymatic detection of the same target analyte can be performed using the functionalized microneedle electrode 120.

In some embodiments of the microneedle sensor device 100, for example, the microneedle electrode 120 can be functionalized with a carbon paste-based functionalization material 125 for non-enzymatic detection of a target analyte, while the microneedle electrode 130 can be functionalized with a carbon paste-based functionalization material 135 for enzymatic detection of the same target analyte. In such case, direct (non-enzymatic) detection of the target analyte at microneedle electrode 120 can be carried out using, for example, square-wave voltammetry (SWV), while an enzyme-based biocatalytic detection of the target analyte at microneedle electrode 130 can be performed using, for example, chronoamperometric measurements of a product of an enzymatic conversion of the analyte. Other electrochemical detection modalities or measurement techniques can be employed for detection of the target analyte at any of the working microneedle electrodes 120 and 130 of the sensor device 100. Among the possible electrochemical measurement techniques that can be employed by the sensor device 100 the following ones can be mentioned.

A potentiometric measurement technique is one where the open circuit potential of the electrochemical cell is directly measured. This potential can be measured between a reference electrode (e.g., the reference electrode 110 of the sensor patch 100) and a working electrode (e.g., the working electrode 120 or the working electrode 130 of the sensor patch 100).

The potentiometric measurement technique is contrasted with the amperometric family of measurements that measure current while controlling the cell potential. For example, chronoamperometry is a powerful tool for measuring diffusion-controlled reactions. In chronoamperometry, the potential is stepped at the beginning of a measurement and then remains constant throughout the duration of the measurement. The current that results from this stimulus is plotted as a function of time.

Voltammetry techniques vary the potential as a function of time. The resulting current is plotted as a function of potential. For example, cyclic voltammetry (CV) sweeps the potential of the cell linearly across a voltage range, while a Fast Scan CV (FSCV) technique does this at a faster rate. Square-wave voltammetry (SWV) uses a square wave superimposed over a staircase function to provide a sweeping measurement that provides two sampling instances per potential. As a result of this sampling technique, the contribution to the total current that results from non-faradic currents is minimized. Like CV, the current is plotted as a function of potential.

In some embodiments of the electrochemical microneedle sensor device 100, at least one of the functionalization materials (e.g., 125 and/or 135) of the microneedle working electrodes 120 and 130 can provide bio-affinity-based, e.g., antibody-based, detection (immunosensing) of the same target compound. For example, different antibodies can be used when both functionalization material 125 and functionalization material 135 provide the antibody-based detection capability.

In other example embodiments of the electrochemical microneedle sensor device 100, at least one of the functionalization materials (e.g., 125 and/or 135) of the microneedle working electrodes of the device 100 (e.g., 120 and 130, respectively), can provide aptamer-based detection of the target compound of interest. For example, different aptamers can be used in the functionalization materials 125 and 135 for detection of the same target compound. Aptamers functionalized by a redox reporter molecule (e.g., methylene blue or anthraquinone) specifically and reversibly bind to the compound of interest, upon which a folding in the conformation of the electrode-bound aptamer occurs. This binding-induced folding leads to a change in the electron transfer characteristics of the redox molecule that is corresponding to the concentration of the target compound of interest and is detected using electrochemical techniques such as square wave voltammetry (SWV) implemented for aptamer-functionalized electrodes of the sensor device 100.

Figure 1B:
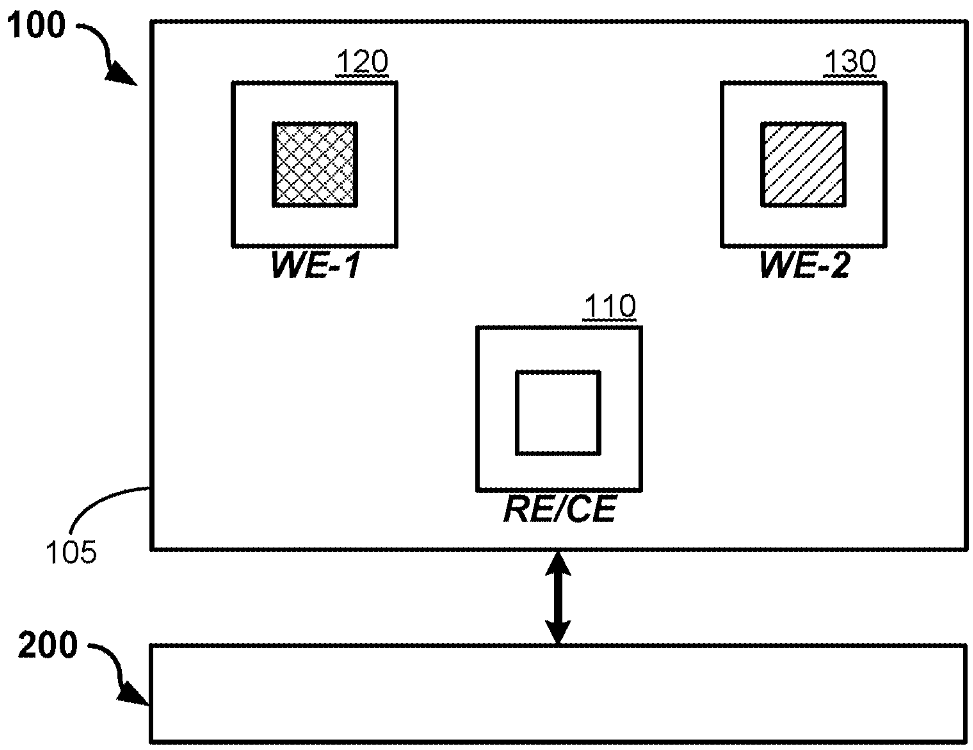
FIG. 1B shows a block diagram depicting an example embodiment of the electrochemical sensor device of FIG. 1A in communication with an electronic device, in accordance with the present technology.

FIG. 1B shows a block diagram depicting an example embodiment of the electrochemical microneedle sensor device 100 of FIG. 1A in communication with an electronic device 200, in accordance with the present technology. In various implementations, for example, the electronic device 200 can affect control, measurement, and monitoring functions, among other functions, of the example sensor device 100 that are related to operation of the example sensor device 100. In some example implementations, the electronic device 200 can be included in an electronics unit of a wearable medical device that incorporates the sensor device 100 or is otherwise interfaced with the sensor device 100. For example, in some embodiments, the electronics unit 200 is configured on the same substrate 105 as the sensor device 100, allowing for an all-in-one sensor patch to be implemented for accurately detecting a concentration of an analyte (e.g., a drug) using parallel, multi-modal detection.

Figure 1C:
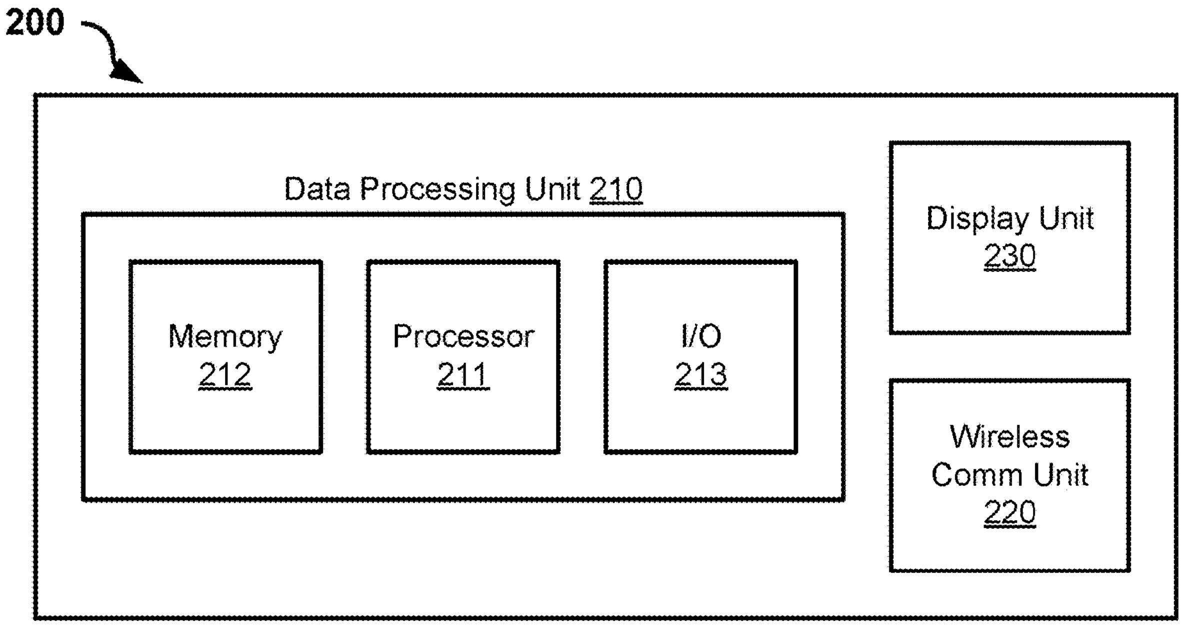
FIG. 1C shows a block diagram of an example embodiment of the electronic device shown in FIG. 1B in accordance with the present technology.

FIG. 1C shows a block diagram of an example embodiment of the electronic device 200. For example, the electronic device 200 can be configured to be electrically coupled to at least one electrode of the sensor device 100. For example, the electronic device 200 can be configured to receive and process electric signals (e.g., voltage, current) produced by the at least one electrode of the sensor device 100. For example, the electronic device 200 can be further configured, based on the signals obtained by the device 200 from one or more electrodes of the sensor device 100 to determine concentration of a target analyte present in the blood, ISF and/or other fluids and/or tissues of a body that are in contact with at least one electrode of the sensor device 100.

In various implementations, the electronic device 200 is operable to store and execute software applications and algorithms to process signals obtained by the electronic device 200 from the sensor device 100 and implement various controls of the sensor device 100, such as application of various voltage waveforms across one or more electrodes of the sensor device 100, according to the technology disclosed in the present application. In various embodiments, the electronic device 200 can be implemented as a portable computing device, such as a mobile communications device, such as a smartphone, tablet or wearable device, like a smartwatch, glasses, etc.; and/or the electronic device 200 can be implemented as a stationary computing device, such as a desktop computer. In some embodiments, the electronic device 200 uses its wireless communications unit 220 for the purpose of data transfer to another device as well as for receiving data (e.g., voltage profiles to be applied across one or more electrodes of the sensor device 100 during its operation).

In some embodiments, the electronic device 200 includes a data processing unit 210 which includes a processor 211 to process data, a memory 212 in communication with the processor 211 to store data, and an input/output unit (I/O) 213. In some embodiments, the I/O unit 213 is electrically interfaced with at least one electrode of the device 100. In some implementations, the I/O 213 includes an analog-to-digital (ADC) converter that converts an electric signal (e.g., current or voltage) received by the I/O 213 from an electrode of the device 100 into a digital form suitable for processing by the processor 211 and/or storage inside the memory 212. In some implementations, the I/O 213 includes a digital-to-analog (DAC) converter that, for example, converts a digital waveform obtained by the processor 211 from the memory 212 into a voltage waveform that is applied across an electrode of the device 100 to implement, using the electrode, one of the electrochemical measurement techniques described above or any other electrochemical detection technique. In some embodiments, the I/O unit 213 can interface the processor 211 and/or the memory 212 to other modules, units or devices, including other external computing devices.

For example, the processor 211 can include a central processing unit (CPU) or a microcontroller unit (MCU) or a graphics processing unit (GPU). For example, the memory 212 can include and store processor-executable code, which, when executed by the processor, configures the data processing unit 210 to perform various operations, e.g., such as receiving information, commands, and/or data, processing information, commands, and/or data, and transmitting or providing information, commands, and/or data to another device.

In some implementations, the electronic device 200 can transmit raw or processed data to a computer system or communication network accessible via the Internet (referred to as 'the cloud') that includes one or more remote computational processing devices (e.g., servers in the cloud).

To support various functions of the data processing unit 210, the memory 212 can store information and data, such as instructions, software, values, images, and other data processed or referenced by the processor 211. For example, various types of Random Access Memory (RAM) devices, Read Only Memory (ROM) devices, Flash Memory devices, and other suitable storage media can be used to implement storage functions of the memory 212.

In some embodiments, the data processing unit 210 includes a wireless communication unit 220, such as a wireless transmitter to transmit stored and/or processed data or a wireless transceiver (Tx/Rx) to transmit and receive data. The I/O 213 of the data processing unit 210 can interface the data processing unit 210 with the wireless communications unit 220 to utilize various types of wired or wireless interfaces compatible with typical data communication standards, for example, which can be used in communications of the data processing unit 210 with other devices, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, NFC (Near Field Communication), and parallel interfaces.

In some embodiments, the data processing unit 210 includes or is otherwise interfaced with a display unit 230, which can include a visual display such as a display screen, an audio display such as a speaker, or other type of display or combinations thereof.

The I/O 213 of the data processing unit 210 can also interface with other external interfaces, sources of data, data storage devices, and/or visual or audio display devices, etc. to retrieve and transfer data and information that can be processed by the processor 211, stored in the memory 212, or exhibited on an output unit (e.g., display unit 230) of the electronic device 200 or an external device. For example, the display unit 230 can be configured to be in data communication with the data processing unit 210, e.g., via the I/O 213, to provide a visual display, an audio display, and/or other sensory display that produces the user interface of a software application. In some examples, the display unit 230 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Figure 1D:
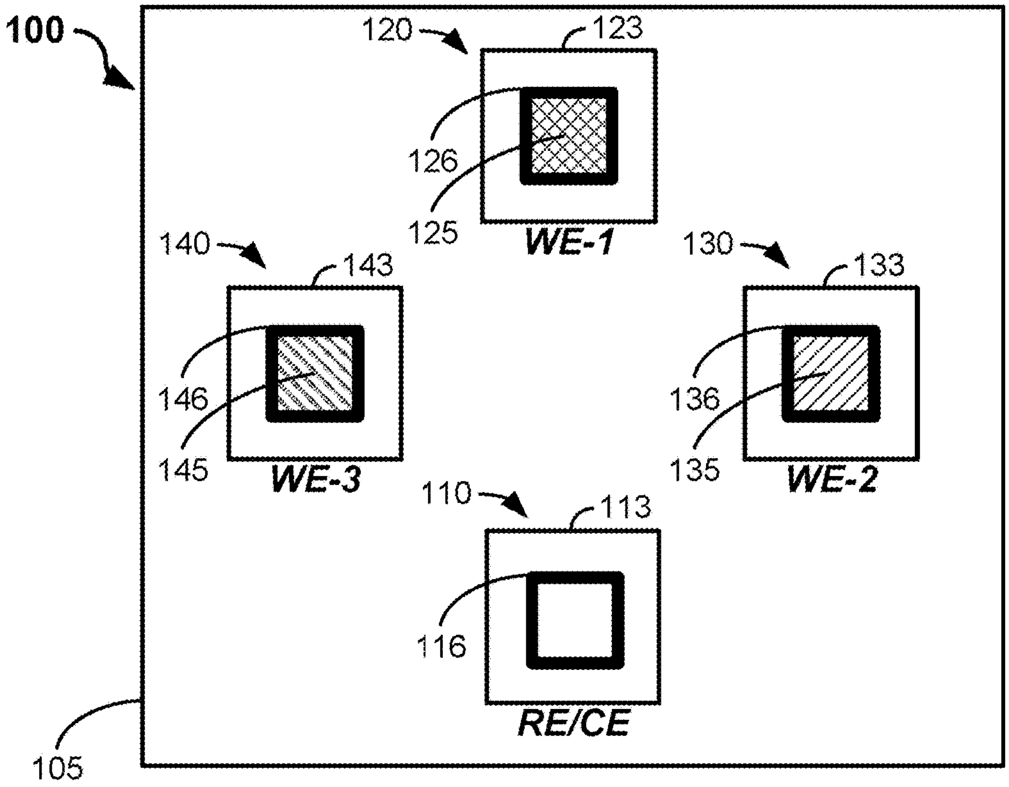
FIG. 1D shows a block diagram depicting an electrochemical microneedle sensor device having at least three microneedle-based working electrodes for parallel, simultaneous, and orthogonal sensing of a single analyte in accordance with the present technology.

FIG. 1D shows a block diagram depicting another example embodiment of the electrochemical microneedle sensor device 100 having at least three microneedle-based working electrodes for parallel, simultaneous, and orthogonal sensing of a single analyte in accordance with the present technology, in which the three microneedle-based working electrodes are disposed on a substrate proximate a reference and/or counter microneedle-based electrode. As shown in the block diagram, the device 100 can include a first microneedle electrode 110 configured as a reference electrode, RE, and/or counter electrode, CE, for electrochemical sensing of the analyte, disposed on substrate 105. The device 100 can include a second microneedle electrode 120 configured as a first working electrode, WE-1, a third microneedle electrode 130 configured as a second working electrode, WE-2, and a fourth microneedle electrode 140 configured as a third working electrode, WE-3, each disposed on the substrate 105. The microneedle electrodes 110, 120, 130, and 140 of the electrochemical microneedle sensor device 100 include the microneedle structure and the electrode probe structure, as previously described. The diagram of FIG. 1D shows microneedle structures 113, 123, 133 and 143 of the microneedle electrodes 110, 120, 130, and 140, respectively. In various example embodiments, the electrode probe structure is disposed within the interior or cavity of the respective microneedle structure. The diagram of FIG. 1D shows electrode probe structures 116, 126, 136, and 146 of the microneedle electrodes 110, 120, 130, and 140, respectively.

In some embodiments, for example, depending on the electrochemical sensing technique to apply at the particular working electrode, the second microneedle electrode 120, the third microneedle electrode 130, and the fourth microneedle electrode 140 can include one or more functionalization materials. In FIG. 1D, the second microneedle electrode 120 includes a functionalization material 125 disposed on or integrated with at least a portion of the electrode probe structure 126 and/or within the opening or cavity of the microneedle structure 123. Similarly, in some embodiments, the third microneedle electrode 130 includes a functionalization material 135 disposed on or integrated with at least a portion of the electrode probe structure 136 and/or within the opening or cavity of the microneedle structure 133. Also, in some embodiments, the fourth microneedle electrode 140 includes a functionalization material 145 disposed on or integrated with at least a portion of the electrode probe structure 146 and/or within the opening or cavity of the microneedle structure 143.

The functionalization materials 125, 135, and 145 of the microneedle sensor device 100 depicted in FIG. 1D can include any of the functionalization materials described earlier or any other functionalization materials suitable for detection of the same target analyte (e.g., L-Dopa or glucose) at any of the functionalized electrodes 120, 130, and/or 140 using any of the electrochemical measurement techniques described above. For example, the functionalization material 125 can include a graphene film, the functionalization material 135 can include carbon (e.g., graphite) powder along with a binder (such as oil) and an enzyme that is specific to the target analyte, while the functionalization material 145 can be a carbon paste-based functionalization material having catalytic metal nanoparticles embedded in it to enhance a detection signal using a non-enzymatic type of detection of the target analyte. Note that all functionalization materials 125, 135, and 145 are tailored for detection of the same target analyte (e.g., L-Dopa or glucose).

For example, in some implementations, the functionalization material 135 can include an aptamer designed to have a conformation that receives the analyte in the biofluid, e.g., L-Dopa in ISF, such that an aptamer-analyte binding complex causes a conformational change of the functionalization material 135 that is detected at electrode 130 as an electrical signal.

Figure 1E:
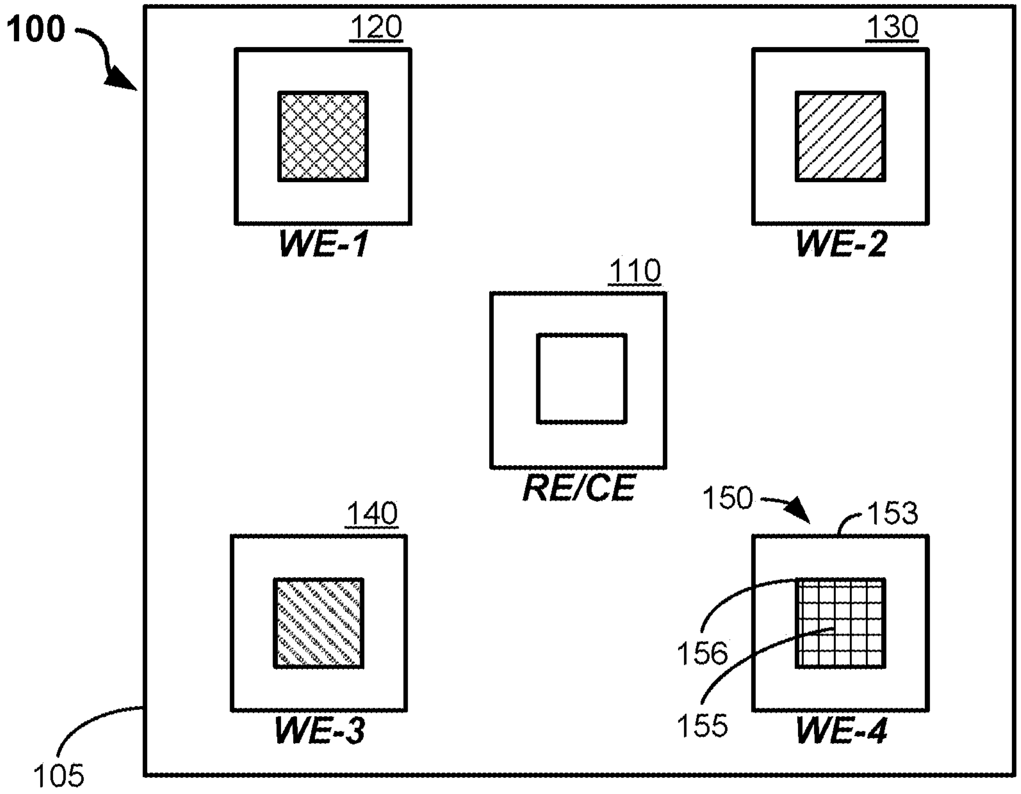
FIG. 1E shows a block diagram depicting an electrochemical microneedle sensor device having at least four microneedle-based working electrodes for parallel, simultaneous, and orthogonal sensing of a single analyte in accordance with the present technology.

FIG. 1E shows a block diagram depicting another example embodiment of the electrochemical microneedle sensor device 100 having at least four microneedle-based working electrodes for parallel, simultaneous, and orthogonal sensing of a single analyte in accordance with the present technology, in which the four microneedle-based working electrodes are disposed on a substrate proximate a reference and/or counter microneedle-based electrode. As shown in the diagram of FIG. 1E, the device 100 can include a first microneedle electrode 110 configured as a reference electrode, RE, and/or counter electrode, CE, for electrochemical sensing of the analyte, wherein the electrode 110 is disposed on substrate 105. The device 100 can include a second microneedle electrode 120 configured as a first working electrode, WE-1, a third microneedle electrode 130 configured as a second working electrode, WE-2, a fourth microneedle electrode 140 configured as a third working electrode, WE-3, and a fifth microneedle electrode 150 configured as a fourth working electrode, WE-4, each disposed on the substrate 105. The microneedle electrodes 110, 120, 130, 140 and 150 of the electrochemical microneedle sensor device 100 include the microneedle structure and the electrode probe structure, as previously described. The diagram of FIG. 1E shows microneedle structures 113, 123, 133, 143, and 153 of the microneedle electrodes 110, 120, 130, 140 and 150, respectively. In various example embodiments, the electrode probe structure is disposed within the interior or cavity of the respective microneedle structure. The diagram of FIG. 1E shows electrode probe structures 116, 126, 136, 146, and 156 of the microneedle electrodes 110, 120, 130, 140 and 150, respectively.

In some embodiments, for example, depending on the electrochemical sensing technique applied at the particular working electrode, the first working electrode 120, the second working electrode 130, the third working electrode 140, and the fourth working electrode 150 can include one or more functionalization materials. In FIG. 1E, the first working electrode 120 includes a functionalization material 125 disposed on or integrated with at least a portion of the electrode probe structure 126 and/or within the opening or cavity of the microneedle structure 123. Similarly, in some embodiments, the second working electrode 130 includes a functionalization material 135 disposed on or integrated with at least a portion of the electrode probe structure 136 and/or within the opening or cavity of the microneedle structure 133. Also, in some embodiments, the third working electrode 140 includes a functionalization material 145 disposed on or integrated with at least a portion of the electrode probe structure 146 and/or within the opening or cavity of the microneedle structure 143. Similarly, in some embodiments, the fourth working electrode 150 includes a functionalization material 155 disposed on or integrated with at least a portion of the electrode probe structure 156 and/or within the opening or cavity of the microneedle structure 153.

The functionalization materials 125, 135, 145, and 155 of the microneedle sensor device 100 depicted in FIG. 1E can include any of the functionalization materials described above or any other functionalization materials suitable for detection of the same target analyte (e.g., L-Dopa or insulin) at any of the functionalized working electrodes 120, 130, 140, and/or 150 using any of the electrochemical measurement techniques mentioned above. For example, the functionalization material 125 can include a graphene film, the functionalization material 135 can include carbon (e.g., graphite) powder along with a binder (such as oil) and an enzyme that is specific to the target analyte, while the functionalization material 145 can be a carbon paste-based functionalization material having catalytic metal nanoparticles embedded in it to enhance a detection signal using a non-enzymatic type of detection of the target analyte. Note that all functionalization materials 125, 135, 145, and 155 can be tailored for detection of the same target analyte (e.g., L-Dopa or insulin). For example, the functionalization material 125 can be a carbon paste-based one for non-enzymatic detection of the target analyte, while functionalization material 135 can be a carbon paste-based one for enzymatic detection of the same target analyte. Furthermore, the functionalization material 145 of the electrode 140 can enable antibody-based detection of the target analyte, and the functionalization material 155 of the electrode 150 can provide aptamer-based detection of the target analyte.

In an example implementation where the functionalization material 155 is configured to facilitate an electrochemical immunoassay (e.g., including label-free immunoassays) to detect a concentration of the analyte in the biofluid, e.g., such as an analyte in ISF. In some embodiments, the electrochemical microneedle sensor device 100 having at least three or four microneedle-based working electrodes for parallel, simultaneous, and orthogonal sensing of a single analyte includes a microneedle structure in which the functionalized working electrodes 140 and/or 150 are disposed in the hollow interior that is formed as a channel spanning between two openings of the microneedle structure. Within the channel, the immunoassay working electrode is functionalized with the functionalization material 155 that includes a capture antibody (e.g., anti-analyte capture and/or detection antibody) covalently connected to a self-assembled monolayer (SAM) coupled to the electrode probe. The channel allows fluid (e.g., ISF) to flow through the channel within the microneedle structure's interior where the functionalized immunoassay electrode contingent is present to facilitate the detectable reaction. In some example implementations, the anti-analyte antibody-functionalization material 155 can interact with the target analyte for detection at the working electrode (e.g., after covalent attachment of the analyte (e.g., insulin) to the capture antibody and/or subsequent binding of a detection antibody). The immunoassay reaction can cause an electrical signal to be detected at the electrode 150.

Figure 1F:
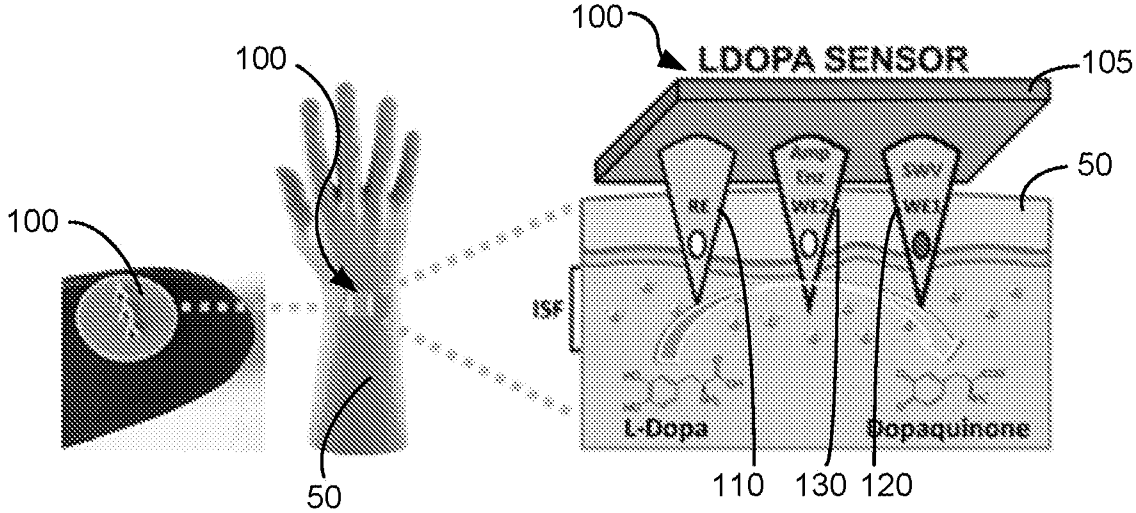
FIG. 1F shows an illustrative diagram depicting an example embodiment of the electrochemical microneedle sensor device of FIG. 1A interfaced with the skin of a subject.

FIG. 1F shows an illustrative diagram depicting an example implementation of the electrochemical microneedle sensor patch 100 for L-Dopa detection having three microneedle electrodes, which is attached and conformed to a hand 50 of a subject wearing the microneedle sensor device 100. The right portion of the diagram illustrates enzymatic and non-enzymatic detection of L-Dopa by microneedle electrode 120 and microneedle electrode 130, respectively. For example, the WE-2 of microneedle electrode 130 is configured to include a functionalization material (i.e., tyrosinase (TYR)) that, when operated for amperometry electrochemical detection, measures the a tyrosinase-based biocatalytic change of L-Dopa to dopaquinone, discussed further below.

Figure 1G:
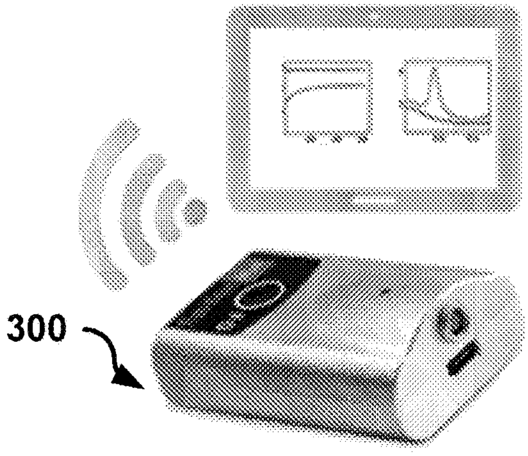
FIG. 1G shows an illustrative diagram of a portable wireless electroanalyzer enabled with wireless data transmission to a smart device in accordance with the present technology.

FIG. 1G shows an illustrative diagram depicting a portable wireless electroanalyzer unit 300 enabled with wireless data transmission to a smart device (e.g., a phone, a tablet, or a computer). The portable electroanalyzer unit 300 can be communicatively coupled to the electronic device 200 interfaced with the microneedle sensor device 100, as described above in relation to FIGS. 1B and 1C, for example. In some embodiments, the portable electroanalyzer unit 300 can include modules of the electronic device 200. As an example, a signal processing unit and a wireless transmitter unit of the electronic device 200 are coupled to the sensor device 100 on the substrate, and a wireless receiver unit and data processing unit is resident on the portable electroanalyzer unit 300 to process the pre-processed or raw sensor data obtained by the sensor device 100. In the example shown in FIG. 1G, the portable electroanalyzer unit 300 includes a display which can display information associated with raw, pre-processed or fully-processed data pertaining to the detected analyte by any or all of the multi-modal microneedle electrode contingents of the microneedle sensor device 100.

Figure 1I:
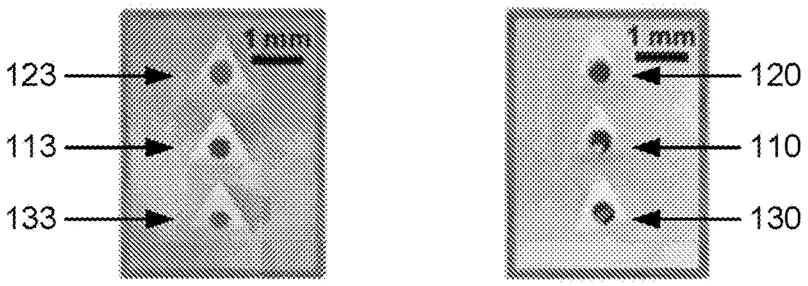
FIG. 1I shows optical images of microneedles in an example embodiment of the electrochemical microneedle sensor device of FIG. 1A before (left) and after (right) packing them with carbon paste.
Figure 1J:
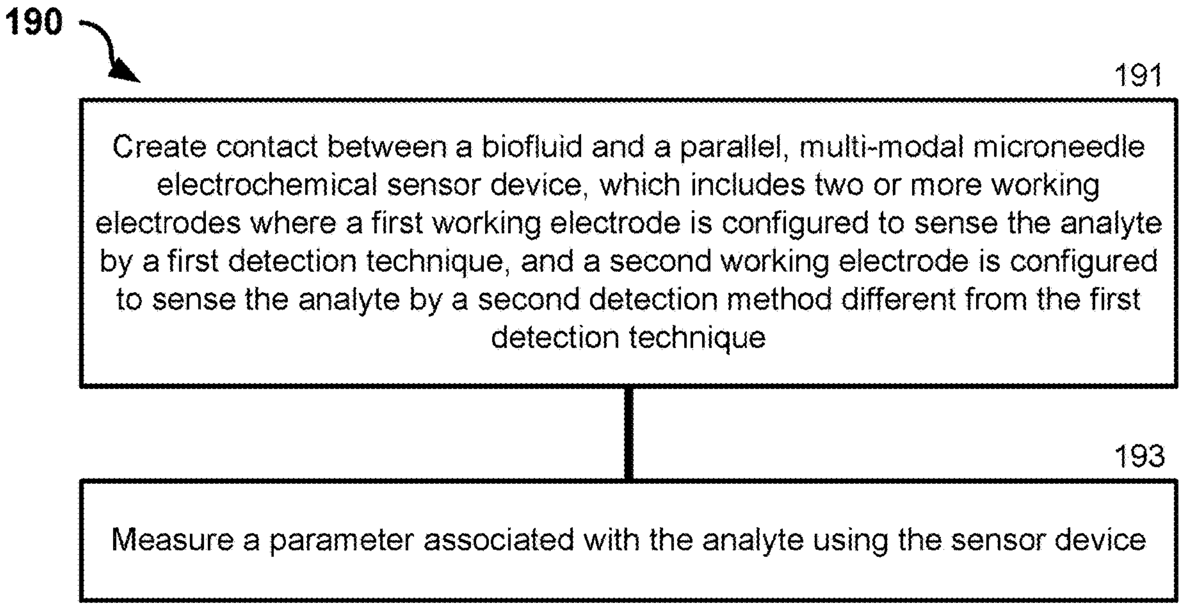
FIG. 1J shows a flow diagram of an example method for parallel, multi-modal electrochemical monitoring of a single analyte to accurately characterize a parameter of the single analyte in the biofluid, in accordance with the present technology.
Figure 1H:
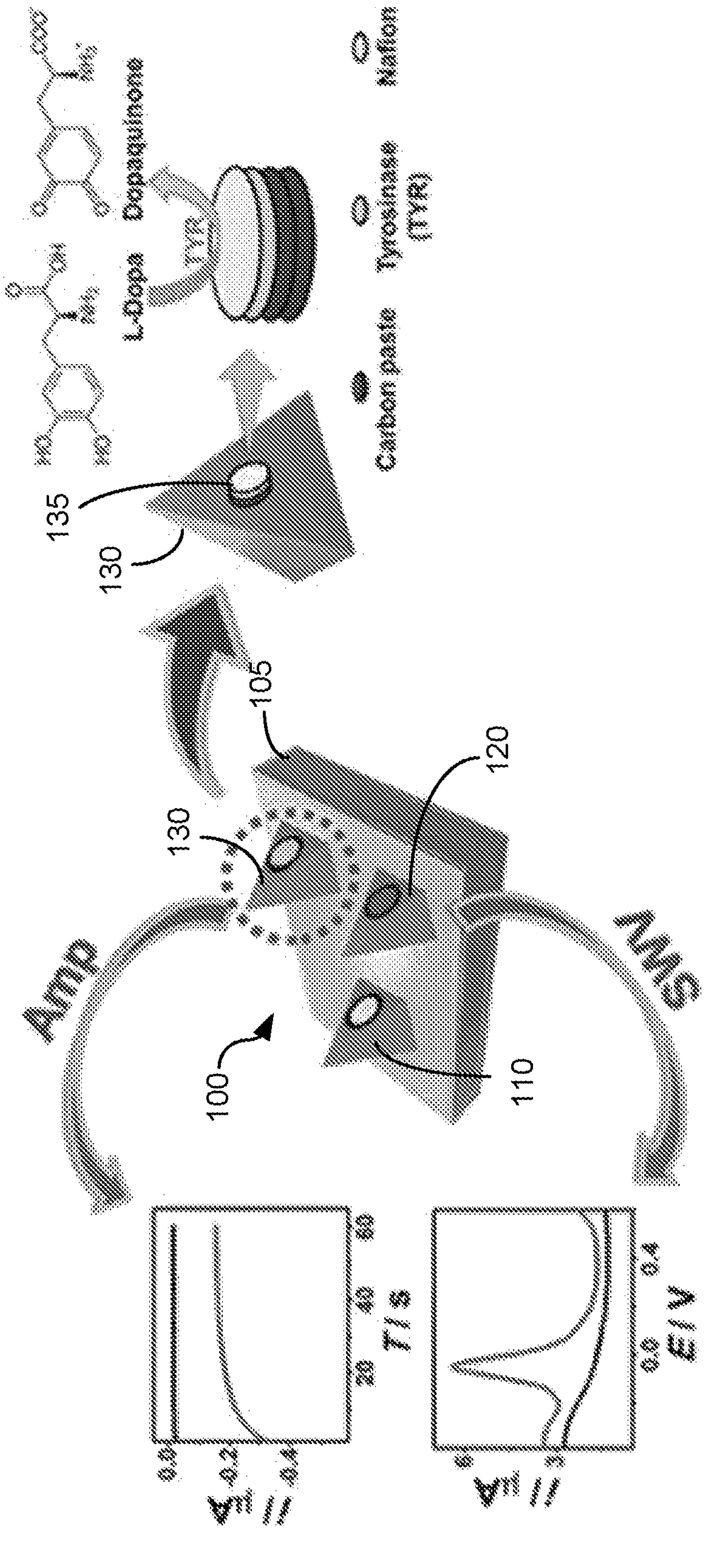
FIG. 1H shows a diagram depicting a 3D view of an example implementation of the electrochemical microneedle sensor device of FIG. 1A.

FIG. 1H shows a schematic of microneedle sensor device 100 illustrating three microneedle-based electrodes for L-dopa sensing using SWV and amperometry at the working electrodes 130 and 120, respectively. FIG. 1H also shows example electrode probe structure and functionalization materials of the microneedle-based working electrode 130 forming reagents layers, including the carbon paste (CP), Tyrosinase enzyme, and Nafion layer.

FIG. 1I shows optical images of microneedle structures 123, 133, and 143 before (left) and after (right) packing with carbon paste-based electrode probe structures to form the electrodes 120, 130, and 140, respectively (scale bar, 1 mm).

As illustrated in FIGS. 1F and 1H, direct (non-enzymatic) anodic L-Dopa detection was carried out using square-wave voltammetry (SWV) using microneedle-based electrode 120, while a tyrosinase-based biocatalytic detection was performed at the neighboring enzyme-functionalized microneedle electrode 130 using chronoamperometric measurements of the corresponding dopaquinone product. Both microneedle working electrodes 120 and 130 offered high sensitivity and selectivity towards the L-Dopa target, along with good stability and a linear current response.

While FIGS. 1F and 1H feature an example biocatalytic microneedle electrode contingent for enzymatic electrochemical detection of L-Dopa, it is understood that the enzymatic microneedle electrode can be configured to detect other target analytes in a biofluid, e.g., on the same or differing sensor devices. For example, in some embodiments, the microneedle sensor device 100 can be configured such that a working electrode microneedle contingent is functionalized with a biocatalyst layer to detect glucose using an enzymatic electrochemical detection technique, where the glucose biosensor working electrode (e.g., microneedle electrode 120) is functionalized to include a glucose oxidase (GOx) layer, which can be fabricated through a layer-by-layer deposition protocol where the enzyme GOx is immobilized inside a permeable polymer film of biopolymer onto the redox mediator.

In some embodiments in accordance with the present technology, a method of monitoring of an analyte in a patient's blood or other fluid or tissue is includes contacting a biofluid (e.g., blood or the other fluid or the tissue containing fluid, such as ISF) with the parallel, multi-modal microneedle sensor device 100, and measuring a parameter associated with the analyte using the senor device 100.

FIG. 1J shows a flow diagram of an example embodiment of a method 190 for parallel, multi-modal electrochemical monitoring of an analyte, e.g., a single analyte like levodopa, carbidopa, glucose, insulin, or other, to accurately characterize a parameter (e.g., concentration) of the single analyte in the biofluid. The method 190 includes a process 191 to create contact between a biofluid and the parallel, multi-modal microneedle electrochemical sensor device 100 (e.g., which includes two or more working electrodes where a first working electrode is configured to sense the analyte by a first detection technique, and a second working electrode is configured to sense the analyte by a second detection method different from the first detection technique, and which includes at least one counter electrode for applying a voltage difference between the at least one counter electrode and at least one of the two or more working electrodes). The method 190 includes a process 193 to measure a parameter associated with the analyte using the sensor device 100.

Example implementations of the example devices, systems and methods were experimented and are described below. The attractive performance and wearable applications of the new microneedle sensor array demonstrated in skin-mimicking phantom gel and upon penetration through a mice skin. Such combination of two (or more) independent detection processes onto a single microneedle platform greatly enhances the available analytical information and offers considerable promise for continuous monitoring of hard-to-detect and/or hard-to-characterize of clinically-critical analytes, such as L-Dopa, and for increasing the power of wearable electrochemical sensors, in general.

The disclosed microneedle based dual-/multi-sensing technique allows extracting further analytical information and leads to a built-in redundancy and cross-check in case of potential interferences on one of the detection modes, sometimes referred to in this disclosure as "orthogonal" sensing. Such "orthogonal" microneedle sensing can be extended for the continuous analysis of other biomarkers present in ISF. Ultimately, the developments described in the following sections will lead to a closed-loop feedback sensor-delivery system that relies on the L-Dopa blood level as a feedback signal for adjusting the L-Dopa dose and will lead to improved treatment and management of PD symptoms and to enhanced patients' quality of life.

Example Implementations of Parallel, Multi-modal Microneedle Electrochemical Sensor Array Devices

Example Materials and Chemicals

In the example implementations described below, the enzyme tyrosinase (e.g., from mushroom, EC 1.14.18.1, 1679 units $mg^{-1}$), 3,4-dihydroxy-L-phenylalanine (L-Dopa), ascorbic acid (AA), uric acid (UA), theophylline, tyrosinase, potassium phosphate monobasic ($KH_2PO_4$), potassium phosphate dibasic ($K_2HPO_4$), sodium chloride, potassium chloride, sucrose, sodium gluconate, Nafion®, calcium chloride anhydrous, magnesium sulfate anhydrous, albumin from bovine serum (BSA), γ-globulins from bovine blood and mineral oil were obtained from Sigma-Aldrich and ethyl alcohol was obtained from Decon Labs (Austin, USA). Agarose was obtained from MCB reagents (Cincinnati, Ohio), and graphite powder (crystalline 99%) was obtained from Alfa Aesar (Ward Hill, MA) and used without further modification.

Example Instrumentation, Procedure and Microneedle-Array Fabrication

In the example implementations, electrochemical measurements (SWV and chronoamperometry) were performed using a PalmSens EmStat3 hand-held potentiostat controlled by PSTrace software version 5.5. Microneedle photographs were taken by using a digital camera (Nikon, D7000). Square-wave voltammetric and chronoamperometric experiments were carried out in a 0.1 M PB solution (pH 7.4) and artificial ISF solution. The L-Dopa stock solutions were prepared in PB. SWV was carried out over the potential range −0.4 to 1.0 V (vs. Ag/AgCl) for 30 s. Chronoamperometry experiments were carried out for a time period (e.g., 60 s) using an applied potential, e.g., 0.1 V (PB solution) or 0.3 V (for artificial ISF). The L-Dopa sample solution (30 μl droplet) was placed on the surface of the inverted microneedle electrode array throughout the electrochemical measurements.

In the example implementations, the microneedle electrodes were prepared in the following manner. For example, the trilateral base of the microneedle sensor was configured to contain 1×3 hollow microneedle arrays, which were in a pyramidal shape. The height of the hollow microneedles (e.g., base to apex) was 1500 μm, and the diameter was 425 μm. A vertical cylindrical hole was intentionally kept at one side of the pyramid microneedle structure. The interstellar between each microneedle array was kept 1 mm.

In some example implementations described herein, L-Dopa sensing was carried out using a three hollow microneedle array. In the example implementations described below, two of these hollow microneedles were packed with a freshly prepared carbon paste (CP), i.e., with an unmodified paste in the WE1 (the non-enzymatic microneedle electrode, in this example), and with an enzyme-containing paste in the WE2 (the enzymatic microneedle electrode, in this example). The third electrode was modified with an Ag wire and used as a reference electrode (RE). In these example implementations, each hollow microneedle electrode had a surface area of 0.002 $cm^2$.

The CP used in WE1 was prepared by mixing 65 wt % of graphite powder and 35 wt % of mineral oil. For the enzymatic WE2 preparation, the paste composition included 55 wt % graphite powder, 10 wt % of the tyrosinase mushroom enzyme, and 35 wt % mineral oil. Following the CP packing, the excess paste was carefully removed from the surface using a surgical blade, followed by smoothing the microneedle surface with wax paper. Electrical contacts were established from the rear side of the packed microneedles, by connecting with stainless Cu wires. These wires were attached using conductive silver epoxy ink and cured at 85° C. for 10 minutes before packing and placing fresh paste on the microneedle surface for each experiment.

Example In-Vitro Evaluation Technique

In the example implementations, the electroanalytical performance of microneedle sensor was performed in 0.1 M PB solution (pH 7.4) and artificial ISF (pH 7.4). The artificial ISF solution was prepared. SWV experiments were carried out in the applied potential scan between −0.4 to 1.0 V (vs. Ag/AgCl). Chronoamperometry experiments were performed for 60 s at 0.1 V for PB solution and 0.3 V for artificial ISF. The stability of the enzyme and non-enzymatic microneedle sensors were performed by conducting repetitive experiments of SWV and chronoamperometry experiments for a prolonged period (up to 100 min). The selectivity of both microneedle sensors was tested in the presence of possible interferences, such as ascorbic acid, uric acid, tyrosine and theophylline. During these interference studies, the enzyme and non-enzymatic sensing electrodes were covered with 2 μL of 1% Nafion solution, that led to an anti-interference barrier. Carbidopa (C-Dopa) and L-Dopa cross studies performed on non-enzymatic carbon paste microneedle electrode. Biofouling studies have been carried-out on non-enzymatic microneedle CP electrodes in presence of BSA, ascorbic acid, uric acid and globulin proteins. All other solutions were prepared by using ultra-pure deionized water.

Preparation of Phantom Gel Mimicked Skin

In the example implementations, to mimic the human skin, agarose phantom gel was prepared in the following manner. Initially, 140 mg agarose were dissolved in 10 mL PBS (1.4%) and stirred at 120° C. in a glass vial, until complete dissolution was obtained. Subsequently, the homogenous agarose liquid was poured into the petri dish and allowed to solidify. Subsequently, three solutions containing different L-Dopa concentrations were dispensed onto the individual petri dishes and were allowed to diffuse for 60 min at room temperature. During the phantom hydrogel experiments, the microneedle sensor array was tested within the phantom gel, allowing 1 min to contact of the needle tips with the gel followed by the SWV and amperometric detection of the L-Dopa.

Example Ex-Vivo Evaluation

In some example implementations, the utility of the microneedle sensor was examined ex vivo by penetrating mice skin placed on top of an artificial ISF solution containing L-Dopa. The mice skin was collected and stored at −20° C. Later the mice skin specimen was cooled down to room temperature and cut into the small pieces. The microneedle was pierced carefully into the small mice skin pieces. The ex-vivo L-Dopa testing was carried out with a compartment filled with artificial ISF. Then, the mice skin penetrated microneedle was placed on the top of the compartment, allowing the microneedle sensor tips to contact the artificial ISF. SWV and chronoamperometric experiments were subsequently performed using optimal parameters.

Example Design of the Microneedle Sensor Array Used in the Experiments

In the example implementations, an example embodiment of the microneedle sensor device 100 was used, which provided for parallel independent electrochemical measurements of L-Dopa using enzymatic-amperometric measurements and direct (non-enzymatic) square-wave voltammetric detection. An illustration of the example microneedle sensor array device used in the example implementations is shown in FIG. 1F, previously described. One of the hollow microneedle electrodes, labelled as WE1, contained an unmodified carbon-paste voltammetric electrode while the second microneedle, labelled as WE2, contained the enzyme (TYR) modified paste. The Ag wire served as a reference electrode in the two-electrode sensing without a counter electrode. A schematic representation of the enzymatic electrochemical detection technique for monitoring L-Dopa (e.g., chronoamperometry) and of the non-enzymatic electrochemical detection technique for monitoring L-Dopa (e.g., SWV) using the example microneedle sensor array is shown in FIG. 1H, previously described.

In the case of the non-enzymatic sensor contingent, a rapid square-wave scan leads to direct oxidation of the target L-Dopa. In parallel, biocatalytic oxidation of L-Dopa is carried out at the tyrosinase enzyme embedded CP microneedle electrode with the dopaquinone product being detected amperometrically. These pair of orthogonally-measured electrochemical signals (e.g., redox and biocatalytic) can capture and account for potential interferences, such as that of Carbidopa upon the enzymatic sensor (but not on the voltammetric one). Schematic illustration of the biocatalytic reaction of L-Dopa by the immobilized tyrosinase enzyme is presented in FIG. 1H. It is noted that the example Nafion coating, included in the functionalization material of the enzymatic microneedle electrode, serves as a permselective protective layer that imparts high selectivity and stability.

The resulting enzymatic and non-enzymatic microneedle sensors were evaluated first in PB solution (pH 7.4), followed by testing in artificial ISF and in a tissue-mimicking phantom gel.

Example Optimization and Characterization of Microneedle L-Dopa Sensors

In some example implementations, SWV parameters, such as frequency, amplitude and potential step, play an important role while analyzing the electrocatalytic reaction of drug molecules. A wide range of frequencies (10-30 Hz) and amplitudes (10-50 mV) was tested and compared (FIG. 5, panels A and B), with 20 Hz frequency and 0.05 V amplitude offering the most favorable SWV performance of the unmodified carbon-paste microneedle sensor.

Figure 5:
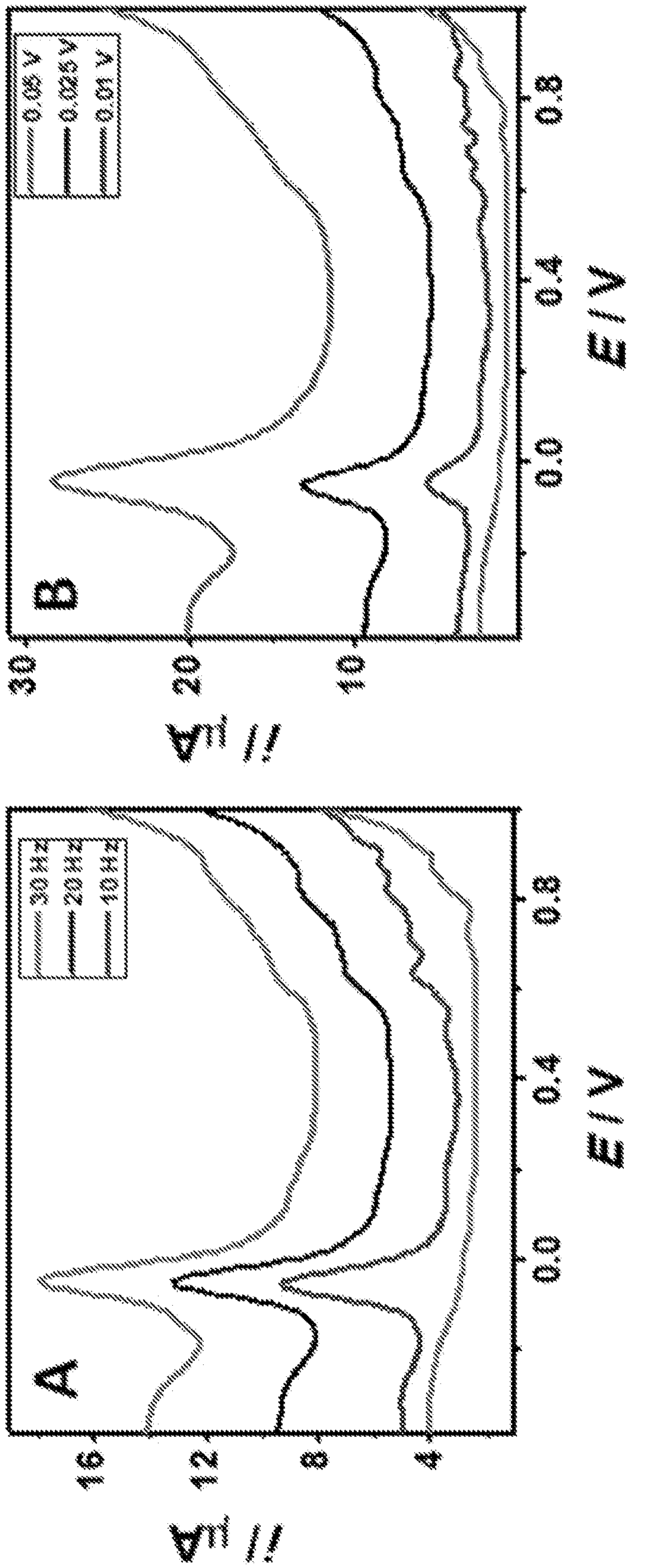
FIG. 5 shows square-wave voltammograms operation and optimization of parameters in accordance with example embodiments disclosed herein.

FIG. 5 shows plots depicting example SWV operation and optimization of parameters. FIG. 5 panel (A) shows a square-wave voltammogram (amplitude 0.025V) for the oxidation of 100 μM L-Dopa in PBS (0.1M, pH 7.4) at different frequencies 10 Hz, 20 Hz and 30 Hz by using microneedle CP electrode. FIG. 5 panel (B) shows a square-wave voltammogram (Frequency 20 Hz) for the oxidation of 100 μM L-DOPA in PBS (0.1M, pH 7.4) at different amplitudes 0.01 V, 0.025 V and 0.05 V by using microneedle CP electrode.

Figure 6:
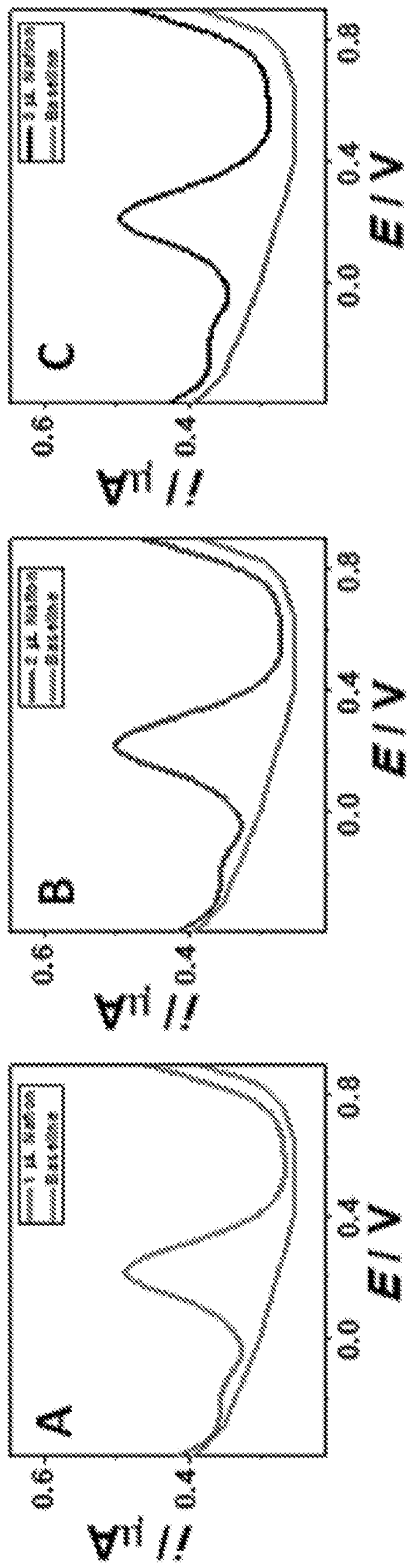
FIG. 6 shows square-wave voltammograms response of L-Dopa oxidation in artificial ISF in accordance with example embodiments disclosed herein.

FIG. 6 shows a panel of example square-wave voltammograms response of oxidation of 50 μM of L-Dopa in artificial ISF, at different volume additions of Nafion (1% w/v), shown in panels (A)-(C) of FIG. 6: (A) 1 μL, (B) 2 μL and (C) 3 μL.

Figure 7:
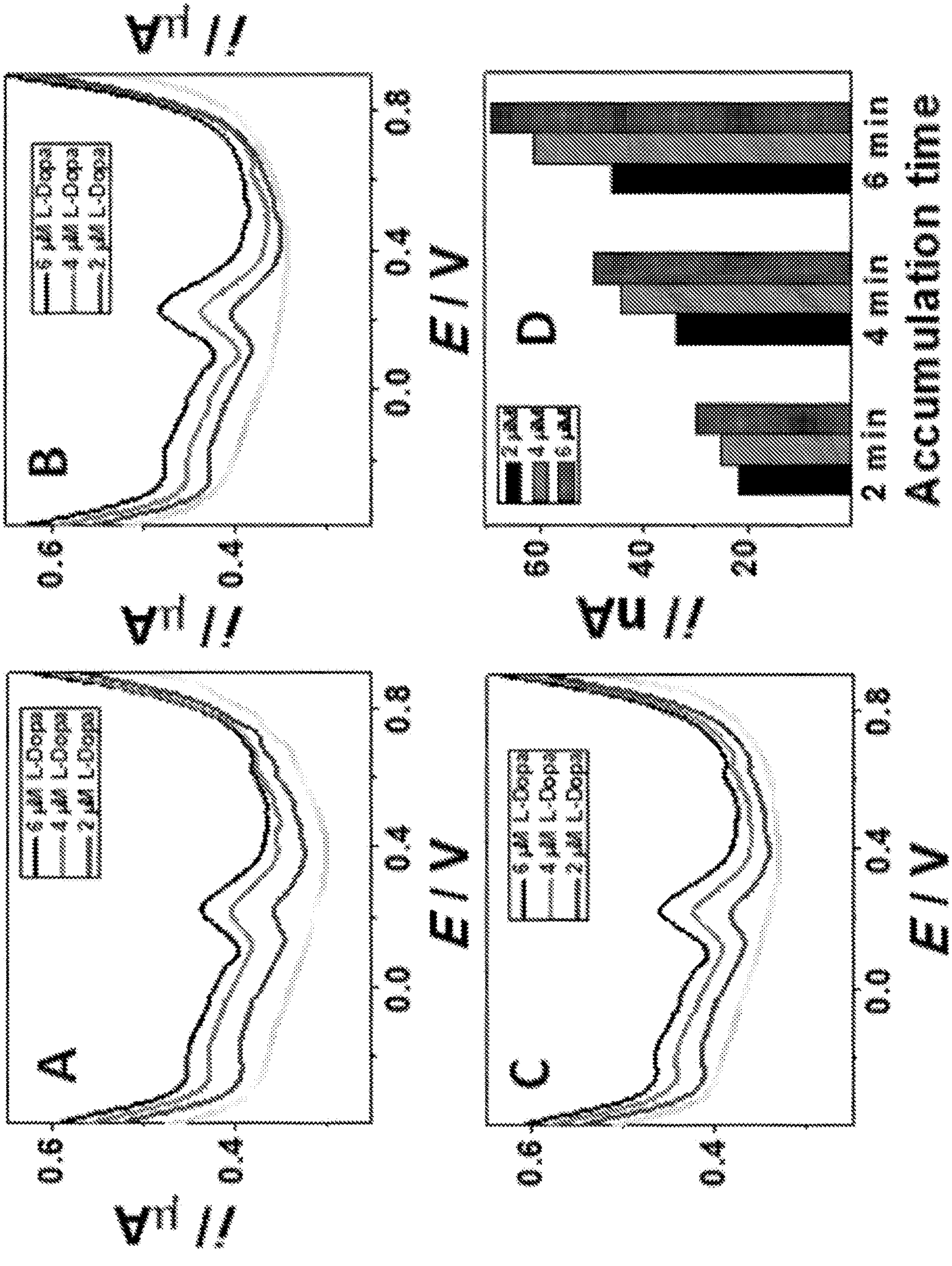
FIG. 7 shows square-wave voltammograms response of L-Dopa microneedle sensors in artificial ISF in accordance with example embodiments disclosed herein.

FIG. 7 shows a panel of example square-wave voltammograms response of the L-Dopa (2, 4 and 6 μM) microneedle sensor in artificial ISF, at different accumulation times, shown in panels (A)-(C) of FIG. 7: (A) 2 min, (B) 4 min, (C) 6 min; and FIG. 7 panel (D) shows corresponding current values with a different accumulation time.

Subsequently, the thickness of the permselective Nafion layer (1% w/v in ethanol) was optimized towards highest sensitivity and selectivity. Different volumes of Nafion (1, 2 and 3 μL) were drop cast on the working electrode surface and recorded the SWV at 50 μM L-Dopa concentrations. As shown in FIG. 6, the oxidation peak current of L-Dopa was higher at 2 μL Nafion coating, compared to the other tested volumes. Subsequently, the experiments were conducted to optimize the accumulation time by performing the SWV scans following 2, 4 and 6 min incubation. The example results, shown in FIG. 7, indicate that the anodic peak current increases upon increasing the accumulation time, reflecting electrostatic interaction with the coating. Subsequent analytical experiments were thus carried out using the 2 μL Nafion coating and following a 1 min accumulation.

Figure 8:
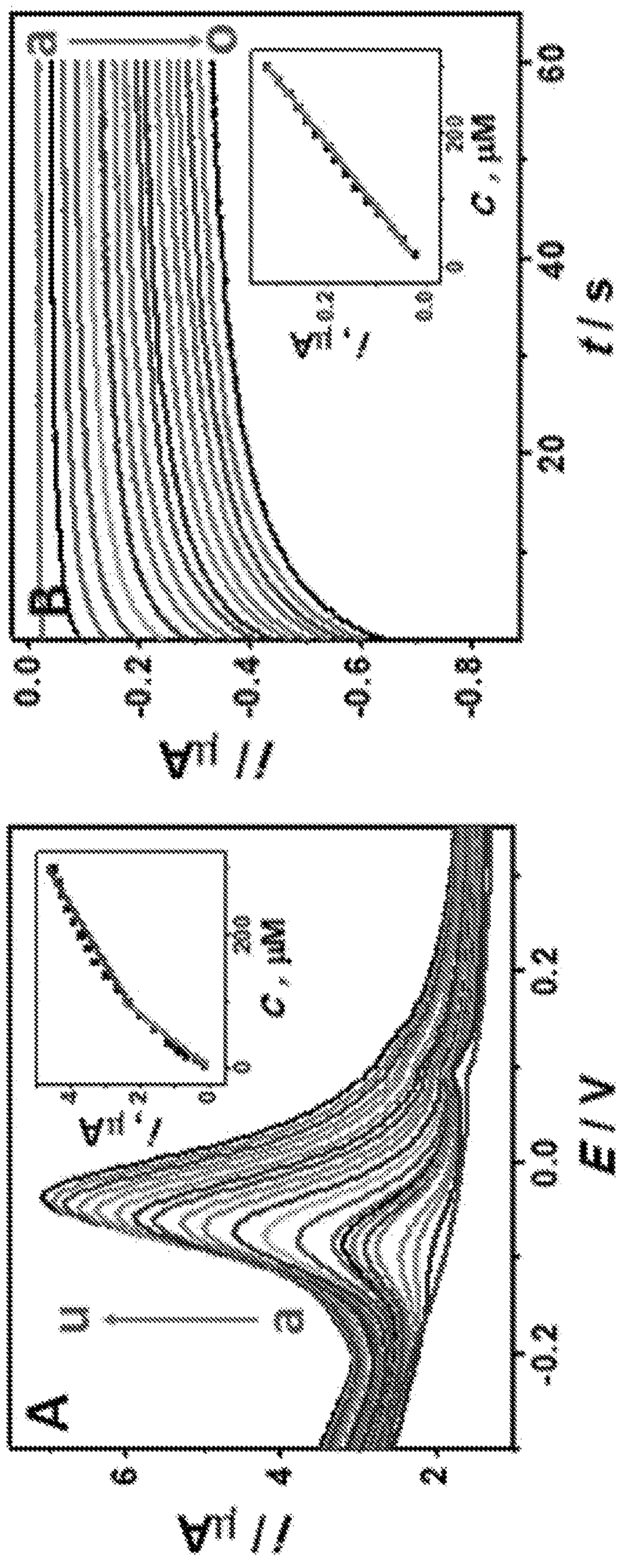
FIG. 8 shows square-wave voltammograms for L-Dopa in PBS and chronoamperometry responses of L-Dopa biosensors recorded in PBS in accordance with example embodiments disclosed herein.

FIG. 8 panel (A) shows square-wave voltammograms for L-Dopa in PBS from 5 to 300 μM concentrations in 20 μM increments. The inset of FIG. 8 panel (A) shows the calibration plot of the background-subtracted peak-current vs. L-Dopa concentration. In the example implementations, the following conditions were used: SWV potential range, −0.4-1.0 V vs. Ag/AgCl using a frequency of 20 Hz, and amplitude of 50 mV. FIG. 8 panel (B) shows chronoamperometry responses of the L-Dopa biosensor recorded in PBS from 0 to 300 μM L-Dopa in 20 μM increments at 0.1 V vs. Ag/AgCl electrode. Inset of FIG. 8 panel (B) shows the corresponding calibration plots.

In some example implementations, the analytical performance of the non-enzymatic microneedle sensor was examined towards the detection of L-Dopa by recording SWV in phosphate buffer solution. A broad dynamic range between 5 μM to 300 μM L-Dopa (e.g., FIG. 8, panel (A)) was tested. The optimized parameters (potential range, −0.4-1.0 V vs. Ag/AgCl using a frequency of 20 Hz, and amplitude of 50 mV) were used to perform these experiments. As illustrated in FIG. 8, panel (A), a well, defined baseline was obtained followed by distinct voltammograms of L-Dopa oxidation were observed through the calibration range. The L-Dopa oxidation peak was obtained at a very low potential of −0.05 V potential. The resulting calibration plot is shown in the inset of FIG. 8, panel (A). Two linear ranges were observed in the concentration range from 5 to 100 μM and 100 to 300 μM, with a correlation coefficient ($R^2$) of 0.989 & 0.9798, respectively (RSD 4.0%, n=3), that permits an appropriate analysis of these micromolar L-Dopa concentrations. Simultaneously, the analytical response of the enzymatic microneedle biosensor towards L-Dopa was evaluated in the range between 20 to 300 μM by recording the chronoamperometric responses in phosphate buffer. The current was sampled for 60 s at an applied potential of 0.1 V (vs. Ag/AgCl) reference electrode. FIG. 8, panel B displays chronoamperograms for increasing L-Dopa concentrations (20 to 300 μM), along with the corresponding calibration plot (inset). A well-defined amperometric response is observed over the entire concentration range, with high linearity (20 to 300 μM) and a correlation coefficient of 0.998 (RSD=3.3%, n=3). These results showed that the biosensor retains a wide dynamic concentration range.

Figure 2:
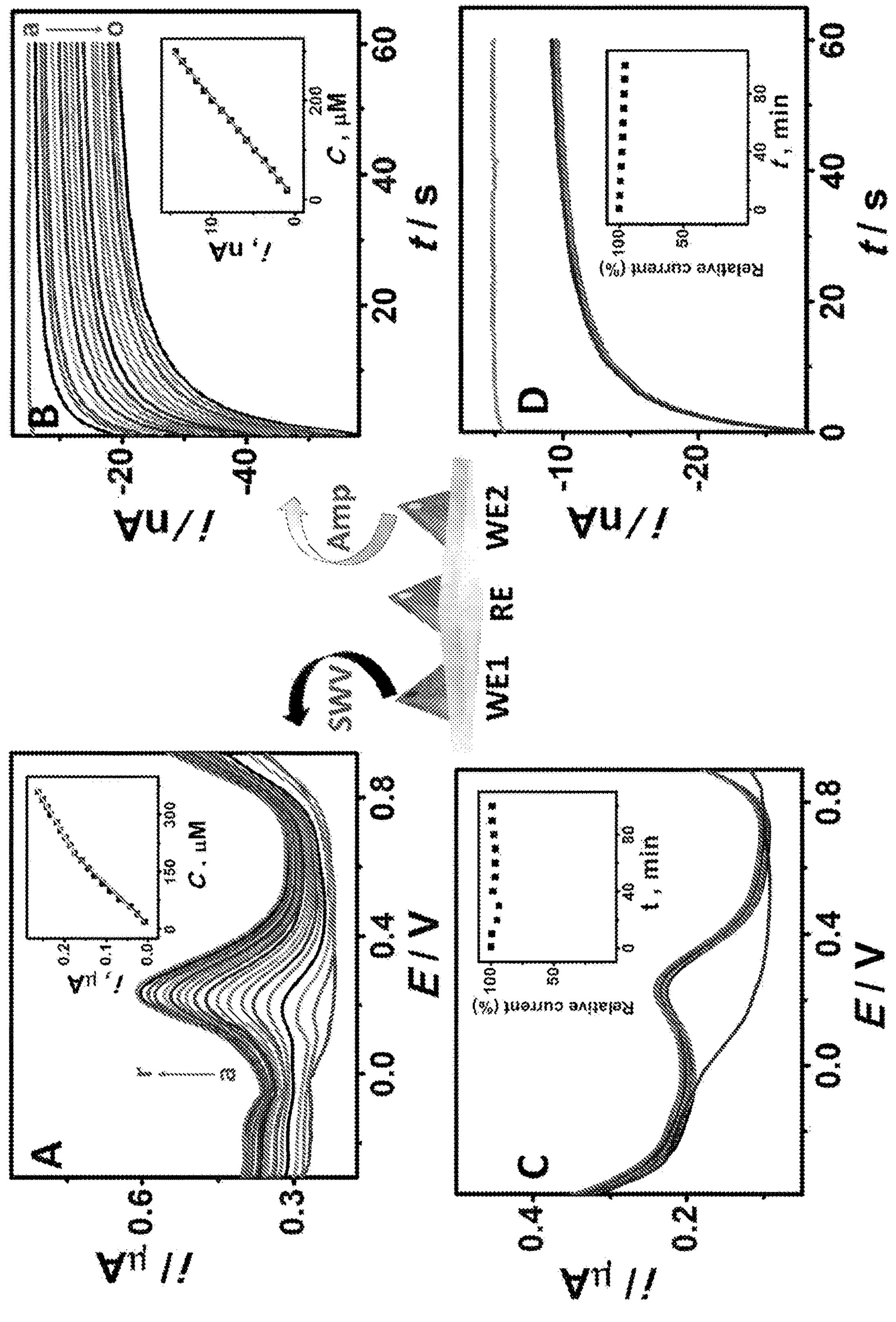
FIG. 2 shows data plots illustrating dual functionality microneedle sensors for L-Dopa detection in accordance with example embodiments disclosed herein.

FIG. 2 shows data plots and a corresponding illustration depicting the example dual functionality microneedle sensors for L-Dopa detection. FIG. 2 panel (A) shows square-wave voltammograms for L-Dopa in artificial ISF, over the f 20-360 μM concentration range with 20 μM increments using the unmodified carbon-paste microneedle sensor; inset shows the resulting calibration plot. Conditions implemented included: SWV potential range −0.4-1.0 V (vs. Ag/AgCl) using 20 Hz frequency, and amplitude of 50 mV.

FIG. 2 panel (B) shows chronoamperometry response of the L-Dopa biosensor recorded in artificial ISF for increasing L-Dopa levels from 20 to 300 μM with 20 μM increments (from "a" to "o") at 0.3 V vs. Ag/AgCl electrode. The inset of FIG. 2 panel (B) shows the corresponding calibration plots. FIG. 2 panel (C) shows a plot depicting example data of the microneedle sensor stability performance using 100 μM L-Dopa in artificial ISF, 10 repetitive measurements were recorded at each 10 min intervals over a period of 100 min. FIG. 2 panel (D) shows a plot depicting example data of the operational stability of microneedle TYR biosensor towards 100 μM L-Dopa in artificial ISF over a 100 min period, with measurements performed at 10 min intervals.

Because continuous monitoring of L-Dopa level is a significant task in the medical diagnosis of Parkinson's patient, and because there is no such existing method hence, the microneedle sensor has been further studied in artificial ISF for the detection of L-Dopa. Both enzyme and non-enzymatic microneedle sensors were analyzed for the continuous evolution of anti-parkinson drug (L-Dopa) in ISF. Non-enzymatic microneedles were tested using the optimal SWV parameters (potential range, −0.4-1.0 V vs. Ag/AgCl using a frequency of 20 Hz, and amplitude of 50 mV). FIG. 2, panel A displays the SWV response for successive additions of 20 μM L-Dopa in artificial ISF, over a wide dynamic range between 20 to 360 μM, along with the corresponding calibration plot (inset). A well-defined L-Dopa oxidation peak is observed with a peak potential of 0.2 V. The anodic peak current increases linearly with the L-Dopa concentration up to 160 μM, followed by a slight curvature at higher concentrations (see inset for the corresponding calibration plot). Additionally, the tested sensor displayed a good reproducibility and sensitivity (0.037 μA/μM) with a correlation coefficient of 0.988 (RSD=3%, n=3).

Good operational stability is a paramount requirement for the minimally invasive microneedle sensors. As illustrated in FIG. 2, panel C, the L-Dopa microneedle sensor offers a highly stable and reproducible SWV response. For example, initial stability test was carried out an over a 110 min period, by recording the SWV response for 100 μM L-Dopa in artificial ISF using 10 min time intervals. A similar response was obtained from each analysis, which signifies a good reproducibility of the sensor performance (S.D.=2.5, n=11). Such a stable and reproducible response supports the exploration of the non-enzymatic SWV microneedle sensor for continuous monitoring of L-Dopa.

The analytical response of the enzymatic microneedle biosensor towards L-Dopa was evaluated first by recording chronoamperometry responses in artificial ISF over the 20 μM to 300 μM range. The current was sampled for 60 s at an applied working potential of 0.3 V (vs. Ag/AgCl reference electrode). FIG. 2, panel B displays the chronoamperometric response of the Tyr-microneedle biosensor for successive 20 μM L-Dopa additions. A well-defined amperometric response is observed over the entire 20-300 μM range. The corresponding calibration plot (shown in the inset) reveals a high linearity over this range, with a sensitivity of 0.048 nA/μM. (R2=0.999, n=3). These obtained responses warrant future possibilities of L-Dopa monitoring in a broad concentration range using Tyrosinase coupled microneedle devices. The L-Dopa microneedle enzymatic sensor offers high reproducibility and stability. The stability test was performed by using a 100 μM L-Dopa in artificial ISF over a 110 min periods, via repetitive measurements at 10 min intervals. As illustrated in FIG. 2, panel D, this experiment resulted in a highly reproducible and stable current response with a standard deviation of 2% (n=11). Such reproducibility demonstrates great promise toward the goal of continuous L-Dopa monitoring using the disclosed microneedle electrochemical sensor devices.

Figure 9:
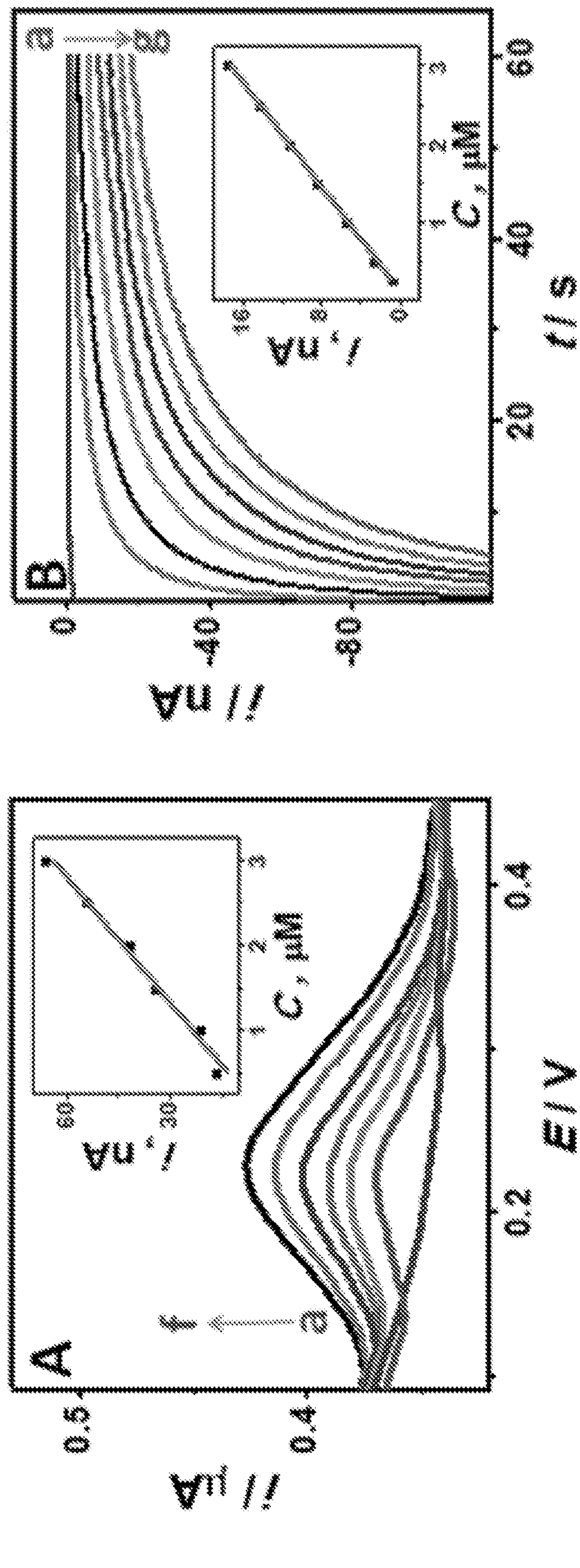
FIG. 9 shows square-wave voltammograms for L-Dopa in ISF and chronoamperometry responses of L-Dopa biosensors recorded in ISF in accordance with example embodiments disclosed herein.

FIG. 9 panel (A) shows square-wave voltammograms for L-Dopa in ISF from 0.5 to 3 μM concentrations in 0.5 μM increments. The inset shows the calibration plot of the background-subtracted peak-current vs. L-Dopa concentration. SWV potential range, −0.4-1.0 V vs. Ag/AgCl using a frequency of 20 Hz, and amplitude of 50 mV. FIG. 9 panel (B) shows chronoamperometry responses of the L-Dopa biosensor recorded in ISF from 0.25 to 3 μM in 0.5 μM increments at 0.3 V vs. Ag/AgCl electrode. The inset in the data plots of FIG. 9 shows the corresponding calibration plots.

The example data in FIG. 9 depicts an example evaluation of the detection limit for L-Dopa sensor, which was evaluated using the non-enzymatic SWV microneedle sensor in artificial ISF solution containing increasing L-Dopa concentrations between 0.5 μM to 3 μM (FIG. 9, panel A). The optimized SWV parameters (potential range, −0.4-1.0 V vs. Ag/AgCl using a frequency of 20 Hz, and the amplitude of 50 mV), optimized experimental conditions (1% Nafion 2 μL; accumulation time, 6 min) were used to perform these experiments. As presented in FIG. 9, panel A, well, defined voltammograms were obtained throughout the tested concentration range. The L-Dopa oxidation peak was obtained at 0.21 V potential. The corresponding calibration plot for L-Dopa detection was displayed in FIG. 9, panel A, inset. Dynamic linear ranges were observed in the concentration range between 0.5 to 3 μM with a correlation coefficient of 0.9875 (RSD 4.5%, n=3). A detection limit of around 0.5 μM was estimated based on the signal-to-noise (S/N=3) response.

The analytical quantification of the enzymatic microneedle biosensor towards L-Dopa was evaluated by recording chronoamperometry responses in artificial ISF solution having the concentration range between 0.25 μM to 3 μM (FIG. 9, panel B). The current was sampled for 60 s at an applied working potential of 0.3 V vs. Ag/AgCl reference electrode. FIG. 9, panel B displays chronoamperogram for increasing the L-Dopa concentrations (0.25 to 3.0 μM), along with the corresponding calibration plot (inset). The entire range of concentrations, well-defined amperograms were observed. The current increases linearly with the increase in the concentration of L-Dopa and a correlation coefficient of 0.999 (RSD=3.2%, n=3). A detection limit of around 0.25 μM was estimated based on the signal-to-noise (S/N=3) characteristics of the response.

Figure 3:
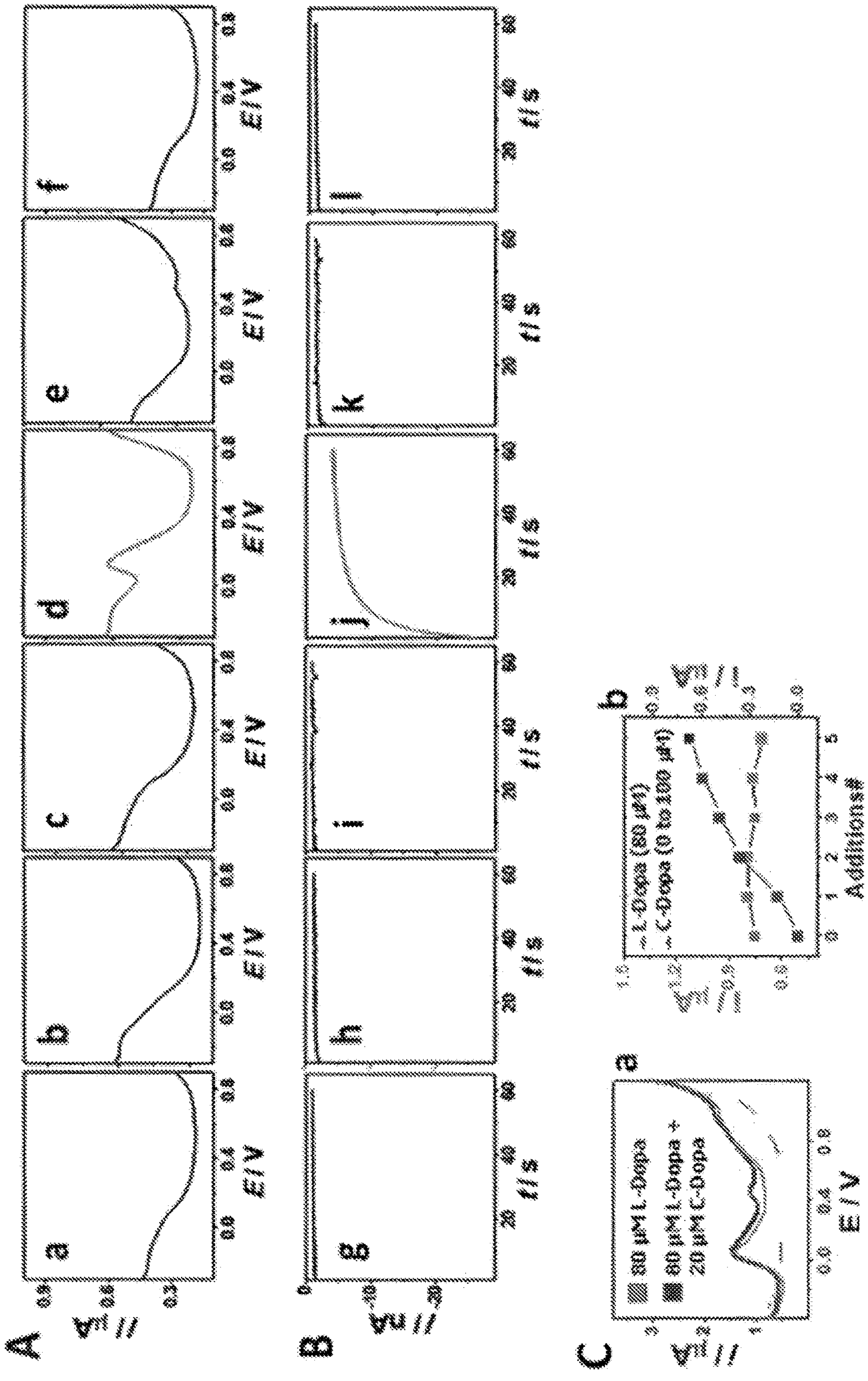
FIG. 3 shows data plots illustrating selectivity of dual-mode microneedle sensors towards L-dopa detection in the presence of potential interferences in accordance with example embodiments disclosed herein.

FIG. 3 shows a panel series data plots depicting the selectivity of the dual-mode microneedle sensor towards L-dopa detection in the presence of potential interferences in accordance with some embodiments disclosed herein. FIG. 3 panel (A) shows square wave data plots, and FIG. 3 panel (B) shows amperometric response data plots, of the L-Dopa microneedle in artificial ISF. In FIG. 3 panels (A) and B, the plots show: baseline (a, g), ascorbic acid (b, h), uric acid (c, i), L-Dopa (d, j), Tyrosine (e, k), and Theophylline (f, l). The concentration of L-Dopa is 50 μM and other interferences are 150 μM. FIG. 3 panel (C) shows L-Dopa and C-Dopa cross-talk studies, where plot (a) shows square-wave voltammograms for 80 μM L-Dopa (red colour) and 20 μM C-Dopa+80 μM L-Dopa (blue colour) in artificial ISF, and plot (b) shows calibration plots of the background-subtracted peak-current vs. L-Dopa concentration (red), background-subtracted peak-current vs. C-Dopa concentration (blue). SWV potential range, −0.4-1.0 V (vs. Ag/AgCl) using a frequency of 20 Hz, and amplitude of 50 mV.

Specific detection of the target drug is vital for realizing reliable L-Dopa detection in the presence of potential co-existing interferences. In some example implementations, the selectivity of the microneedle sensor array was evaluated by examining the response of both the enzymatic and non-enzymatic microneedle electrodes to possible co-existing interferences, such as ascorbic acid, uric acid, tyrosine and theophylline using artificial ISF medium (FIG. 3). This testing was carried out using 50 μM of L-Dopa in the presence of three-fold higher concentrations (150 μM) of the potential interfering compounds. As indicated from FIG. 3, panel A (a-f), the unmodified microneedle carbon-paste electrode displays a highly selective SWV response in the presence of an excess of all other potential interferences. As illustrated in FIG. 3, panel B (g-l), the enzyme-based microneedle biosensor displays similar high selectivity towards L-Dopa detection, with its amperometric response not affected by the presence of these potential interferences. It should be pointed out that operating the non-enzymatic paste microneedle amperometrically (at +0.2V), instead of the SWV mode, offered also selective detection of L-Dopa in the presence of these interferences (not shown). In all cases, the high selectivity of these microneedle sensors reflects the combination of a low operating potential with a perm-selective Nafion layer that rejects negatively-charged species such as ascorbic acid and uric acid (and along with the specific bio-catalytic reaction, in the case of the enzyme microneedle sensor).

C-Dopa is an important administrated drug, often used as an inhibitor in PD therapeutic applications along with L-Dopa, with the control ratio of 4:1 (L-Dopa: C-Dopa). C-Dopa is mainly useful to reduce side effects of L-Dopa and subsequently improves the efficiency of therapy which leads to the better control of PD. Hence, it is important to examine the influence of C-Dopa upon the L-Dopa response. Here the orthogonal detection is advantageous as the enzyme-based sensor responds to both drugs. In contrast, the non-enzymatic SWV microneedle sensor allows simultaneous detection of L-Dopa and C-Dopa, e.g., based on their different peak potentials.

In some example implementations, L-Dopa and C-Dopa cross studies were conducted using the unmodified CP microneedle sensor in artificial ISF to evaluate distinct detection of both analytes (FIG. 3, panel C). Upon testing 80 μM L-Dopa, a clear and distinct SWV was observed at 0.1V; subsequent addition of 20 μM C-Dopa resulted in two separate peaks at 0.1V and 0.5V for L-Dopa and C-Dopa, respectively. Later, calibration studies of C-Dopa were carried out in a varied concentration range between 0-100 μM in the presence of L-Dopa (80 μM). The C-Dopa SWV current values were increased linearly with respective additions of concentrations, without affecting the current values of L-Dopa (FIG. 3, panel C). Such high selectivity of L-Dopa in the presence of C-Dopa reflects that the proposed microneedle-sensing platform offers significant promise for the monitoring of PD.

Figure 4:
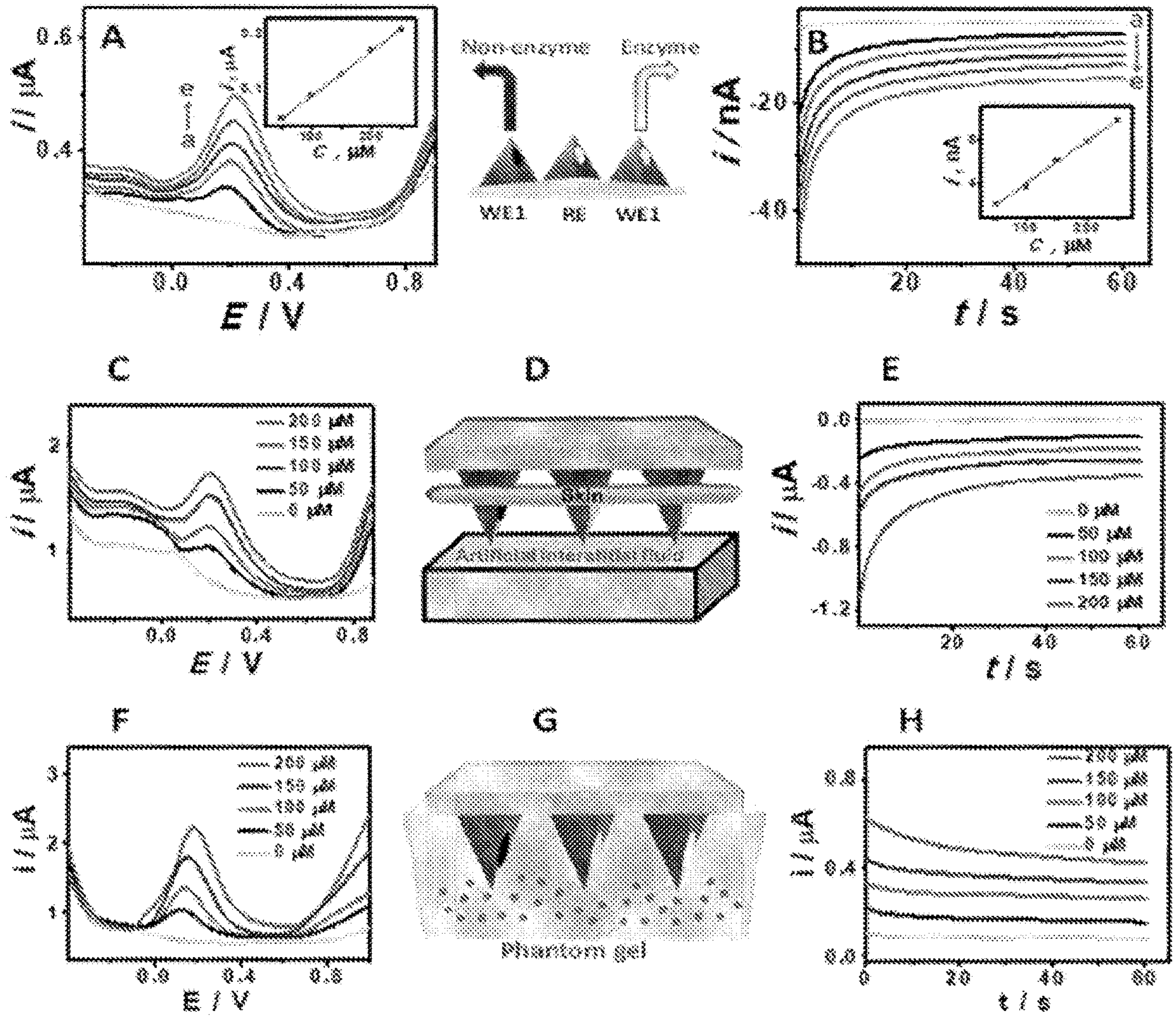
FIG. 4 shows square-wave voltammograms for L-Dopa and chronoamperometry responses of L-Dopa biosensors in artificial ISF using microneedles penetrated through mice skin in accordance with example embodiments disclosed herein.

Example Dual L-Dopa Microneedle Sensing: Phantom Gel Mimicked Skin Model Evaluation, Ex-Vivo Mice Skin and Stability in the Presence of Proteins In some example implementations, after the successful evaluation of individual enzymatic and non-enzymatic microneedle sensors using the different electrochemical techniques (SWV and chronoamperometry), the microneedles were tested by interchanging working sensors alternatively to detect L-Dopa in artificial ISF. The SWV and chronoamperometry experiments were carried out simultaneously on three CP modified microneedle electrodes. The SWV and the chronoamperometric response of both microneedle sensors were recorded simultaneously, upon adding 50 μM L-Dopa to artificial ISF (FIG. 4, panels A and B). Both microsensors WE1 and WE2 display a well-defined response, with current signals proportional to the L-Dopa concentration. Such linearity is indicated from the corresponding calibration plots (see insets), with correlation coefficients of 0.998 and 0.999 (RSD=3%) with the sensitivity of 0.082 μA/μM and 0.038 nA/μM for the SWV and amperometric signals, respectively.

FIG. 4 shows a panel series data plots depicting square-wave voltammograms and chronoamperometry response plots for L-Dopa in ISF in a range of concentrations. In panel (A) of FIG. 4, the plot shows square-wave voltammograms for L-Dopa in ISF from 50 to 250 μM concentrations in 50 μM increments. Inset shows the calibration plot of the background-subtracted peak-current vs. L-Dopa concentration. In panel (B) of FIG. 4, the plot shows chronoamperometry responses of the L-Dopa biosensor recorded in ISF from 50 to 250 μM in 20 μM increments at 0.3 V vs. Ag/AgCl electrode. The inset shows the corresponding calibration plots. FIG. 4 panels (C) and (E) show plots demonstrating real-time L-Dopa detection in artificial ISF through the mice skin penetrated microneedle; FIG. 4 panels (F) and (H) show plots demonstrating SWV and amperometric responses of different L-Dopa concentrations with mimicking skin phantom gel. FIG. 4 panel (D) shows a schematic diagram illustrating the detection of L-Dopa in artificial ISF using the microneedle penetrated through the mice skin; and FIG. 4 panel (G) shows a schematic representation of mimicking skin phantom gel with the penetration of microneedle. The other conditions in the example implementation were as in FIG. 2.

As shown by the example data in FIG. 4, the analytical performance of microneedle sensor array was assessed for L-Dopa detection in artificial ISF in connection to an ex-vivo mice skin model. As shown in FIG. 4, panel D, the microneedle sensor was pierced on to the mice skin to access the target ISF L-Dopa. The L-Dopa level in the artificial ISF compartment was thus increased linearly between 50 and 200 μM, and the corresponding SWV (non-enzyme) and chronoamperometric (enzymatic) measurements were carried out simultaneously. A distinct and well-defined voltammetric and amperometric L-Dopa response, proportional to the drug concentration, is observed, reflecting the suitability of both microneedle electrodes for such through skin sensing (FIG. 4, panels C and E). To mimic future monitoring of PD patients, the microneedle sensor array was evaluated using a tissue (dermis)-mimicking phantom gel skin model involving an agarose (1.4%) hydrogel (FIG. 4, panel G). The microneedle sensor array with its electrode tips located inside the gel. As illustrated in FIG. 4, panels F and H, the phantom-gel experiment yielded well-defined voltammetric and amperometric response for the increasing L-Dopa gel concentrations in 50 μM steps. Overall, such favorable response of both the ex-vivo skin model and the tissue-mimicking phantom-gel results hold considerable promise toward future continuous in-vivo L-Dopa monitoring.

Figure 10:
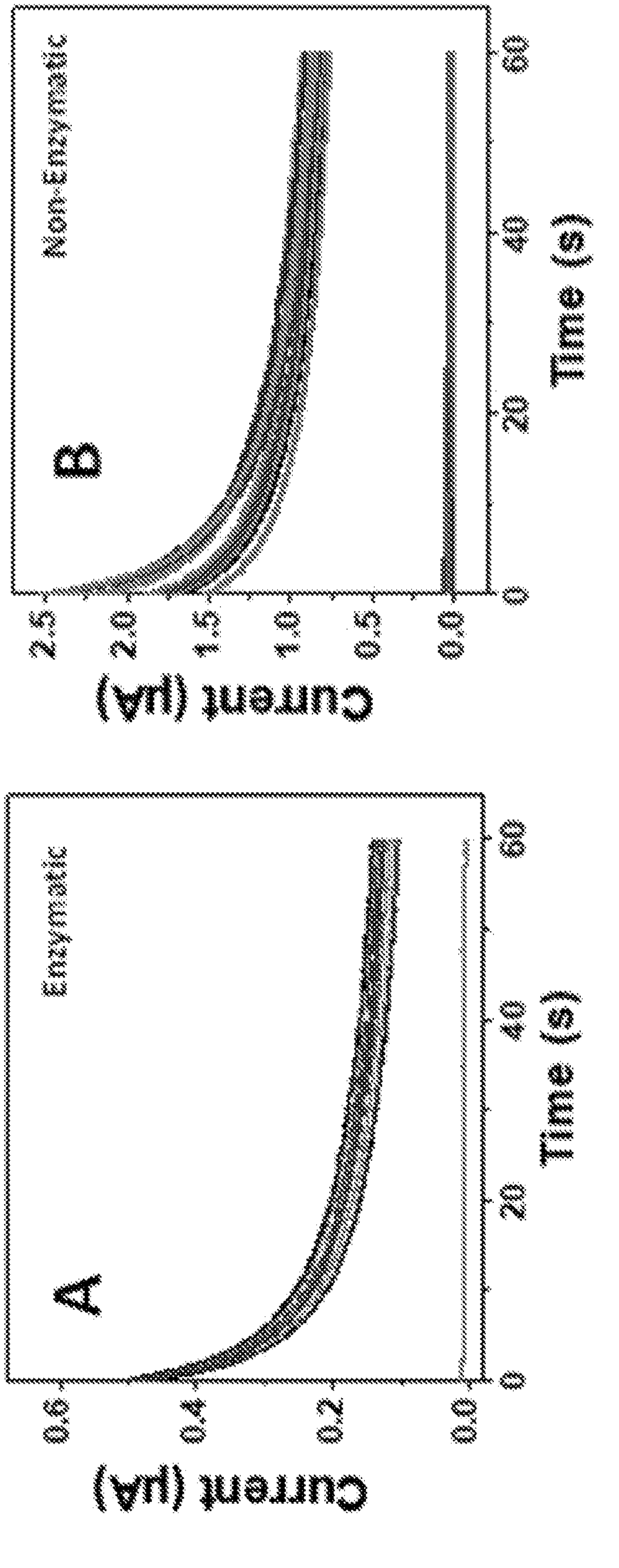
FIG. 10 shows chronoamperometric responses of L-Dopa enzymatic and non-enzymatic sensors recorded in artificial ISF in accordance with example embodiments disclosed herein.

FIG. 10 shows data plots depicting example chronoamperometric responses of the L-Dopa enzymatic sensor (plot A) and the non-enzymatic sensor (plot B) recorded in artificial ISF containing BSA+Globulin (2+0.5 mg mL-1, respectively) and 100 μM L-Dopa at +0.2 V vs. (Ag/AgCl) electrode, over 2 hours period, with repetitive measurements 10 min intervals.

Minimally invasive ISF motoring are commonly subject to surface biofouling due to protein constituents of the ISF. In some example implementations, the surface of the microneedle electrodes was coated with a protective Nafion film to address the biofouling effects. As illustrated in FIG. 10, the sensor stability was tested in the presence of common ISF proteins 2 mg $mL^1$ albumin and 0.5 mg $mL^1$ gamma-globulin. Both tested microneedle sensors displayed a relatively stable response for repetitive measurements at 10 min intervals over a 2 hour period. Despite the presence of the protein fouling agents, only an 11 and 14% decrease of the response of the non-enzymatic and enzymatic microneedle sensors, respectively, was observed over the entire 2 hours experimental period. Current efforts are aimed at minimizing further the protection against biofouling through the combination of additional protective coatings.

Figure 11:
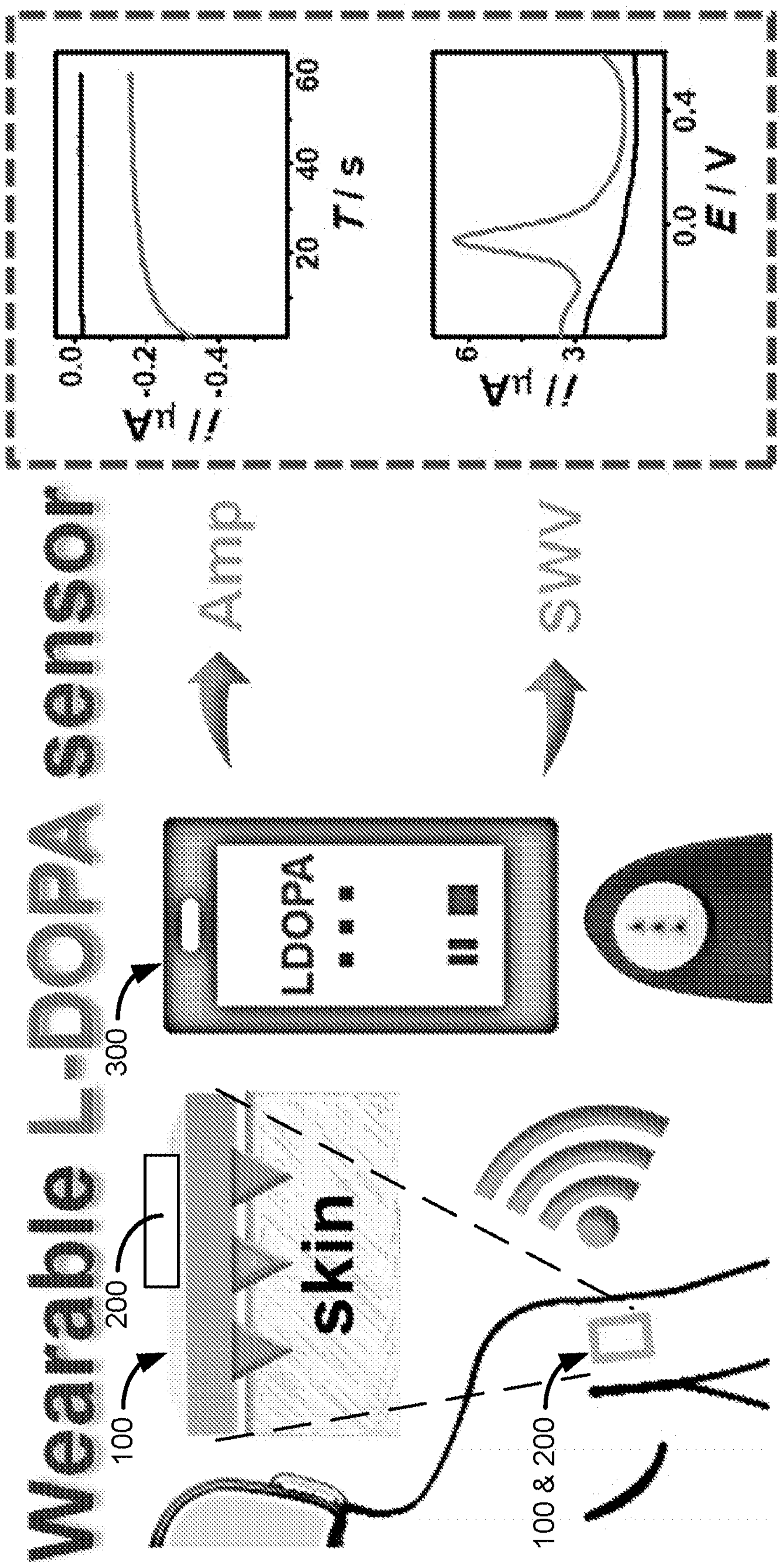
FIG. 11 shows a schematic illustrating a wearable sensor system for monitoring L-Dopa on a patient user in accordance with one embodiment disclosed and described herein.

FIG. 11 shows a schematic illustrating a wearable sensor system containing microneedle sensors for L-Dopa detection in accordance with example embodiments of the disclosed minimally invasive and continuous monitoring sensor and/or actuator technology. The example of FIG. 11 shows an example embodiment of the parallel, simultaneous, multi-modal microneedle sensor device (patch) 100 in wireless communication with a display device 300.

Example embodiments and implementations are disclosed herein providing a wearable chemical sensing platform, based on a microneedle electrode array, for continuous analyte monitoring, such as for the anti-Parkinsonian drug L-Dopa, and are envisioned to provide a new dual-modal sensing approach based on independent electrochemical measurements involving redox and bio-catalytic processes. In various examples described herein, such multi-modal L-Dopa sensing offers a built-in redundancy and enhances the information content of the microneedle sensor arrays. The new orthogonal microneedle sensing can use simultaneous L-Dopa sensing by SWV and chronoamperometry measurements at unmodified and enzyme-modified carbon-paste electrodes, respectively. The example microneedle sensing platform displays an attractive analytical performance in skin mimicking phantom gel as well as upon penetration through a mice skin, with high sensitivity, wide linear dynamic range, good stability, along with high selectivity. The ability to combine several distinct independent processes onto a single wearable platform holds considerable potential for enhancing the power of a wide range of on-body chemical sensing devices, in general, and could be readily extended to the monitoring of other key biomarkers in different biofluids.

Overall, such a dual-modal microneedle L-Dopa sensing platform holds a considerable promise for providing timely feedback on a proper L-Dopa dosing regimen in a decentralized fashion. Such effective real-time L-Dopa monitoring capability would allow optimal dosing and improved management of PD. These example results represent developments towards addressing the urgent need for effective L-Dopa monitoring. Embodiments of the presently disclosed technology could also lead to full integration of the wireless electronic interface and wireless transmission, investigation of effective anti-biofouling protecting coatings and clinical testing and validation in PD patients.

Example Embodiments of Parallel, Multi-Modal Microneedle Electrochemical Sensor Array Devices Interfaced for Closed-Loop Drug Delivery In some aspects, the microneedle sensor array can be integrated in a closed-loop system, containing an L-Dopa pump and a dose-automation algorithm operable on a connected electronic device, which will replace the common intermittent oral administration, towards optimal individualized drug dosing and a greatly improved management of PD symptoms.

Figure 12:
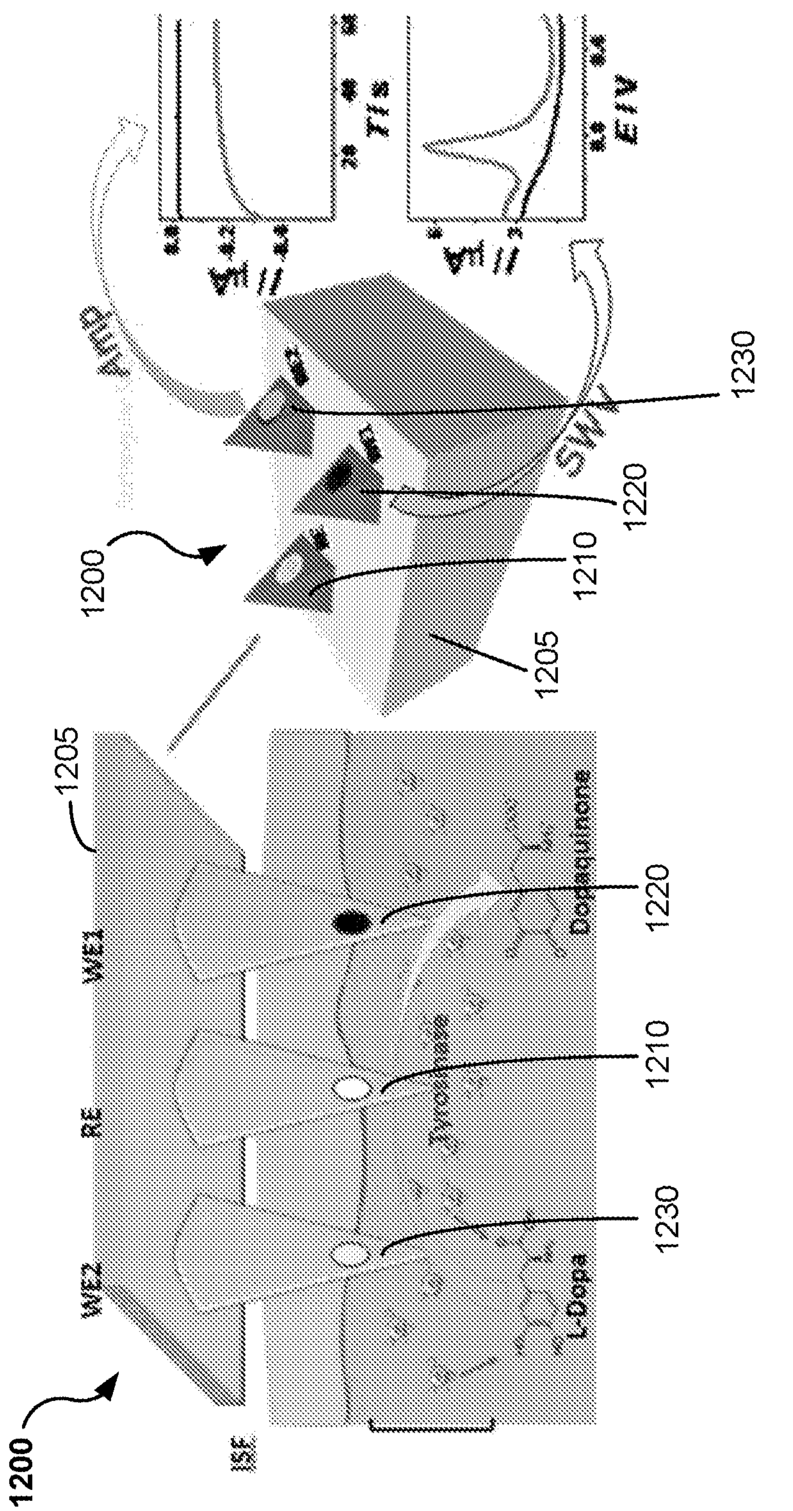
FIG. 12 shows an illustrative diagram depicting an example embodiment of an orthogonal electrochemical microneedle sensor device interfaced with the skin of a subject.

The microneedle sensor array of the example dual-sensing device relies on highly-sensitive and selective dual (e.g., catalytic and enzymatic) electrochemical detection of the drug (L-Dopa) at modified electrode surfaces—for example, at the microneedle tips—based on at least two different detection principles and recognition routes (such as in the example diagram of FIG. 12). Such multi-mode orthogonal detection provides independent measurements and greatly enhances the reliability of the microneedle sensing approach.

FIG. 12 shows an illustrative diagram depicting an example embodiment of an orthogonal (e.g., dual- or multi-modal) electrochemical microneedle sensor device 1200, in accordance with example embodiments of the microneedle sensor device 100, interfaced with the skin of a subject for sub-cutaneous parallel, multi-model measurement of L-Dopa. The left portion of the diagram shows the three microneedle electrodes 1210, 1220, 1230 coupled to substrate 1205 of the sensor 1200, which enable catalytic and enzymatic electrochemical detection of L-Dopa at electrode probes embedded in the microneedle structures. The right portion of the diagram illustrates enzymatic and non-enzymatic detection of L-Dopa by microneedle electrode 1220 and microneedle electrode 1230, respectively. For example, the WE-2 of microneedle electrode 1230 is configured to include a functionalization material (i.e., tyrosinase (TYR)) that, when operated for amperometry electrochemical detection, measures the a tyrosinase-based biocatalytic change of L-Dopa to dopaquinone; whereas the WE-1 of microneedle electrode 1220 is unmodified and can measure the change in current as a function of voltage sweep using voltammetry, e.g. SWV.

The example biocatalytic microneedle biosensor contingent of the device 1200 shown in FIG. 12 relies on the specific oxidation of L-Dopa by the immobilized tyrosinase enzyme and the low-potential cathodic amperometric detection of the biocatalytically generated dopaquinone. The second electrocatatytic voltammetric detection can rely on rapid square-wave voltammetric (SWV) scanning, monitoring the direct L-Dopa oxidation and the corresponding SWV signature.

The catalytic and biocatalytic microneedle electrodes of the example dual-sensing device can be coated with permselective anti-interference films that can improve the selectivity of the L-Dopa detection by excluding potential electroactive interference and fouling macromolecules present in ISF. For example, the permselective anti-interference films can be used to select target L-Dopa molecules against six potentially interfering (electroactive) species: ascorbic acid, uric acid, cysteine, urea, acetaminophen and glycine. For each of the electrodes of the microneedle sensor array (e.g., microneedle sensor device 100), different permselective coatings, e.g., Nafion or poly(o-phenylenediamine) (PPD), can be prepared under different conditions. For example, the electropolymerization conditions of the PPD coating can be used for controlling the pore size, pore density and film thickness, and hence tuning the transport properties of the coating toward rejecting interfering electroactive ISF constituents. For example, Nafion is expected to attract the target L-Dopa electrostatically while rejecting common anionic electroactive interferences (such as ascorbic and uric acids). Anti-interference coating films can also impart the necessary resistance to surface fouling. The protection against surface fouling can be increased by choosing optimal coating electropolymerization conditions (e.g., e.g., polymerization times) to reach optimal antifouling properties of the coating films.

The example dual-/multi-sensing device 1200 can be coupled to flexible electronics, containing, for example, a dual potentiostat for controlling the operation of the microneedle sensors, and transmitting the data in real-time via Bluetooth or other communication channel.

Figure 13:
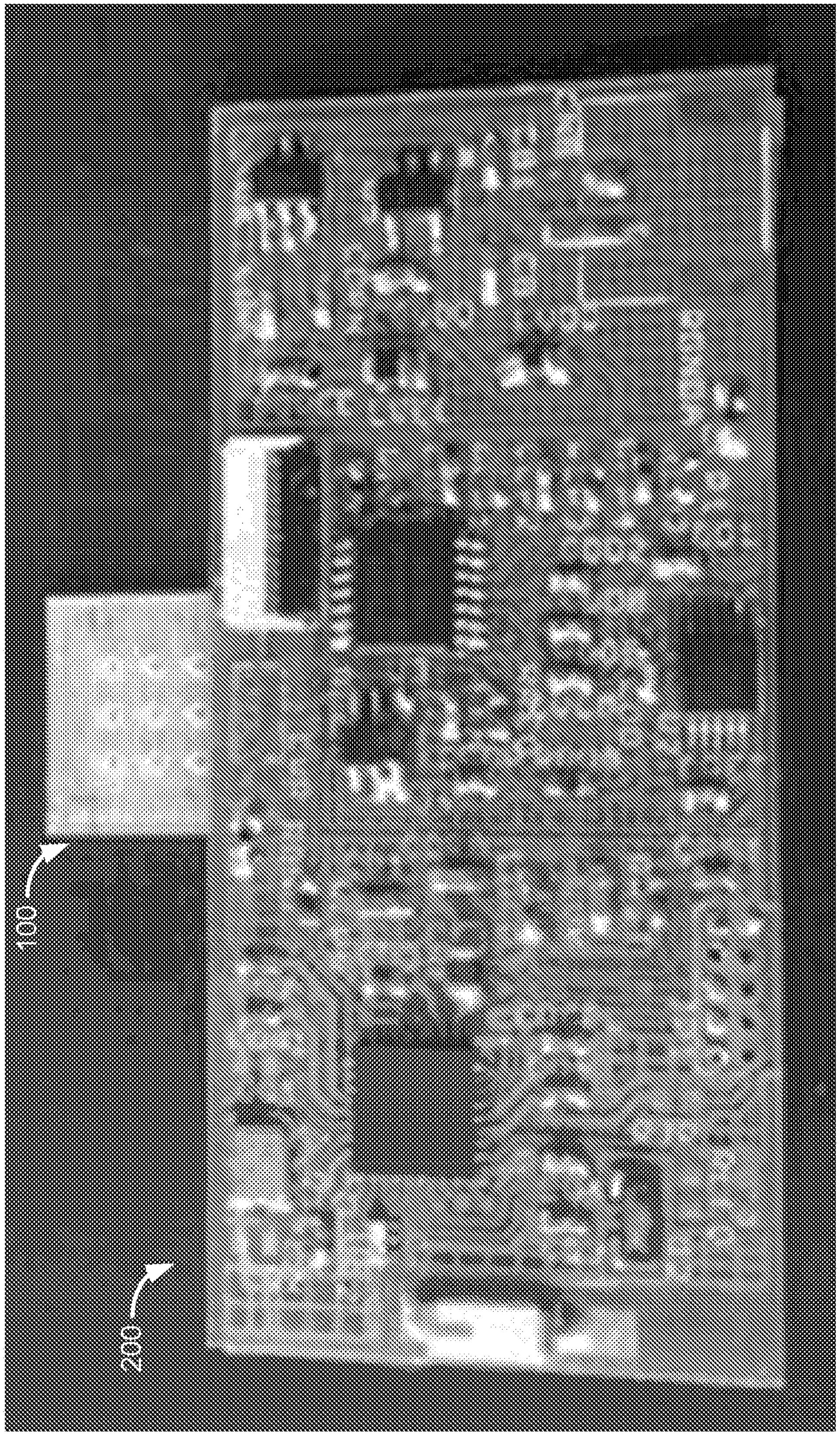
FIG. 13 shows an image showing flexible electronics that can be used with an electrochemical microneedle sensor device in accordance with the disclosed technology.

FIG. 13 shows an image of an example electronic control board, e.g., an embodiment of the electronic device 200, interfaced to an example microneedle sensor patch, e.g., an embodiment of the microneedle sensor device 100, which was used in experimental implementations. The example electronic control board ("e-Board") was used in some of the aforementioned example implementations, where the e-Board was placed proximate (e.g., above) the microneedle array sensor patch, and provided signal processing and electrochemical detection technique circuitry and control, e.g., multi-potentiostat capability.

The example dual-/multi-sensing device 1200 can provide rich electrochemical information towards measurements of the target L-Dopa analyte, e.g., as compared to common single modality sensing routes. In some embodiments, the device includes a two-working electrode microneedle to one-reference/counter electrode microneedle ratio in the microneedle electrode array. The microneedle electrodes can be constructed by packing hollow microneedles with different catalytic and biocatalytic carbon paste (CP) electrode transducers. In some embodiments, carbon-paste composition can include carbon (graphite) powder along with a binder (such as oil). In some embodiments, catalytic metal nanoparticles can be embedded in the carbon paste to enhance the signal. For example, the example carbon-paste electrodes modified with cobalt porphyrin-$TiO_2$ nanoparticles, Pt nanoparticles, Ir nanoparticles, or others, can be used for differential pulse voltammetric detection of L-Dopa.

In some embodiments, for example, the microneedle sensor device 100 (e.g., the example dual-/multi-sensing device 1200) can use solid electrode transducers (e.g., metallic or carbon ones); whereas, in some embodiments, for example, the sensor device 100 can use a coated Pt-wire electrode transducer embedded within a hollow microneedle; yet, in some embodiments, for example, the sensor device 100 can use graphene-film modified gold wire embedded within a hollow microneedle. For the biocatalytic sensor contingent of the microneedle sensor device 100, an enzyme (e.g., tyrosinase) can be modified on a solid transducer via electropolymeric entrapment. Some embodiments of the sensor device 100 can use an enzyme stabilizer.

In some embodiments of the microneedle sensor device 100 (e.g., the example dual/multi-sensing device 1200), the electrocatalytic SWV voltammetric microneedle sensor can use different electrocatalysts known to enhance the L-Dopa detection (e.g., zinc or iron oxides). The electrocatalysts particles can be loaded within the carbon paste. Parameters of the SWV voltammetric operation, including the potential step, amplitude and frequency and the initial and final potentials can be optimized to enhance the L-Dopa detection. In some embodiments of the device, the electrocatalytic SWV voltammetric microneedle sensor employs a cyclic SWV mode of operation which combines oxidative and reductive square-wave voltammetric scans and provides distinct electrochemical fingerprints of target analytes.

Some devices and methods disclosed in the present application can use a correspondence (e.g., a calibration relationship) between blood plasma L-Dopa levels determined, for example, using high-performance liquid chromatography (HPLC) and ISF L-Dopa levels determined using the devices and methods disclosed herein, such as embodiments of the microneedle sensor device 100 and the method 190. The calibration relationship can be established, for example, by correlating or otherwise processing the temporal L-Dopa levels in the blood plasma obtained by, for example, HPLC technique and simultaneous measurements of the ISF L-Dopa levels obtained using a device and/or a method according to the disclosed technology. For example, time profiles for the L-Dopa concentrations in the blood plasma and ISF can be compared, and a time interval between the maximum L-Dopa concentrations in those fluids after L-Dopa administration into a patient can be determined. The established correspondence between the blood plasma and ISF L-Dopa levels can be used to estimate the L-Dopa level in the blood based on a measurement of the L-Dopa concentration in the ISF using the technology disclosed.

Figure 14:
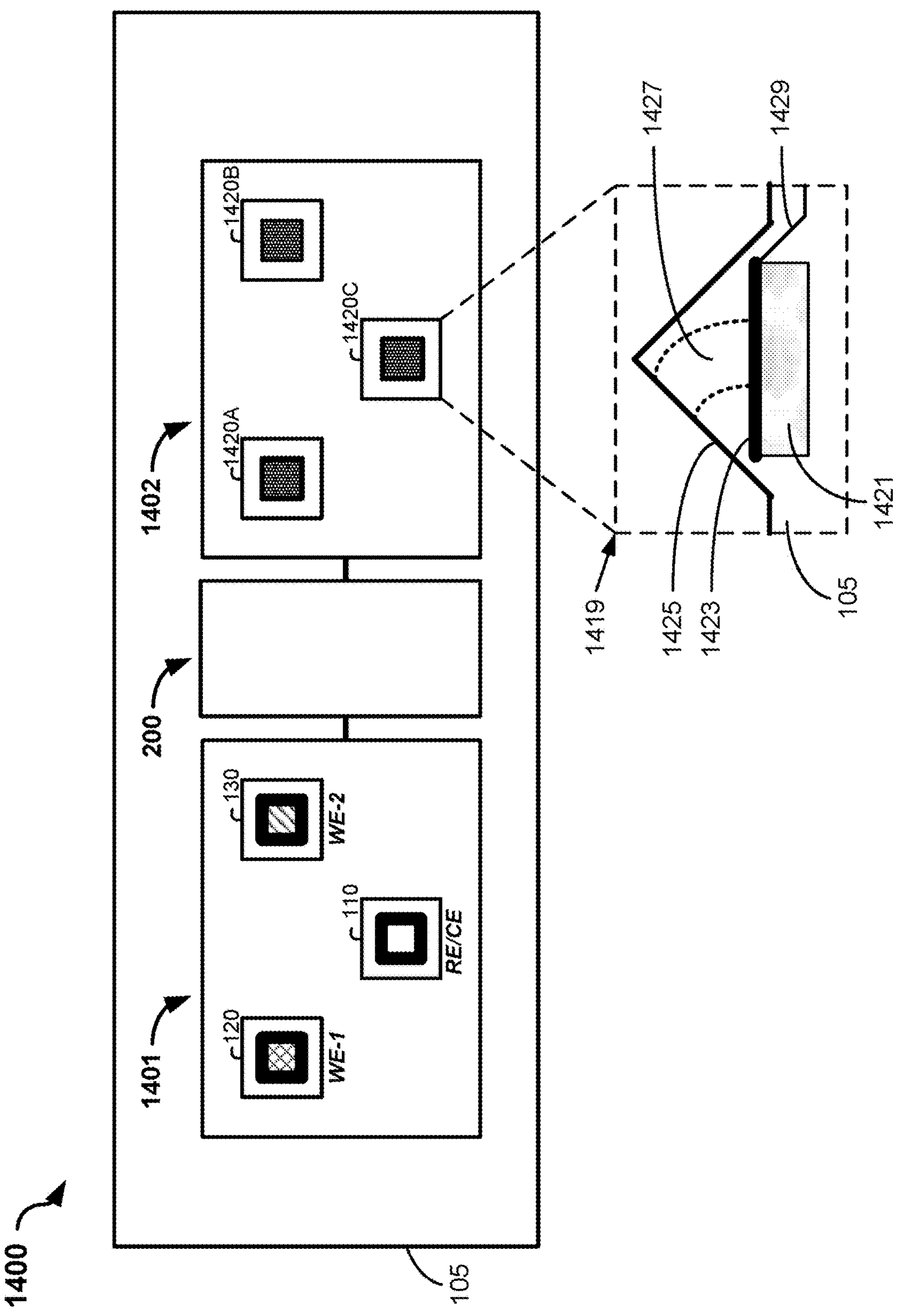
FIG. 14 shows a block diagram of an example embodiment of a closed-loop microneedle drug-analyte sensor and delivery system in accordance with the present technology.

FIG. 14 shows a block diagram of an example embodiment of a closed-loop microneedle drug-analyte sensor and delivery system 1400 in accordance with the present technology. The system 1400 includes the microneedle sensor device 100 interfaced with the electronic device 200 and/or the portable wireless electroanalyzer unit 300, where the microneedle sensor device 100 includes a drug-analyte sensor-based microneedle sensor contingent 1401 to electrochemically detect the drug-analyte in a biofluid (e.g., ISF) and drug-analyte delivery-based microneedle actuator contingent 1402 to controllably-release the drug-analyte into the biofluid in a controlled amount and timing. The system 1400 is a closed-loop feedback sensor-delivery system that uses the estimated drug-analyte level (e.g., L-Dopa concentration level in blood) as a feedback signal for adjusting the dose of the drug-analyte (e.g., L-Dopa) to be delivered (e.g., through subcutaneous delivery from the microneedle structures).

The drug-analyte sensor-based microneedle sensor contingent 1401 can include the microneedle electrodes (e.g., working and counter/reference electrodes) of the microneedle sensor device 100 of any of the aforementioned embodiments, e.g., such as in FIG. 1A, 1D, 1E or other. The drug-analyte delivery-based microneedle actuator contingent 1402 can include one or more microneedle structures 1420A, 1402B, 1420C, . . . on the substrate 105, e.g., arranged proximate to the microneedle electrodes of the sensor contingent 1401. In some embodiments of the actuator contingent 1402, for example, one or more of the microneedle structures of the actuator contingent 1402 include a containment chamber 1421 (e.g., reservoir) that contains a volume of the drug-analyte for controllable release. In this example embodiment, as shown in inset 1419 of FIG. 14, the microneedle structure 1425 is disposed on the substrate 105 and includes the chamber 1421 within the microneedle structure 1425 and/or under the microneedle structure 1425 in the substrate 105. The chamber 1421 is selectively enclosed from the opening of the microneedle structure by a conducting polymer barrier structure 1423, based on permeability and tunable through an autonomous porosity change, which is controlled by the data processing unit of the electronic device 200. In some embodiments, for example, the actuator contingent 1402 can include a micropump can be integrated with the microneedle patch.

For example, the controllable permeability of the polymer barrier 1423 of the microneedle structures 1425 of the actuator contingent 1402 are configured to controllably release and thereby deliver the drug-analyte to the region penetrated by the microneedle structures of the device 100 based on the processed drug-analyte information (detected by the microneedle electrode sensing contingent). The actuator contingent 1402 of the system 1400 can enable the autonomous (closed-loop) delivery of the drug-analyte in a therapeutic intervention in response to the detected concentration of the drug-analyte present in the patient.

In some implementations, for example, the data processing unit of the electronic device 200 processes the detected electrical signals obtained from the sensor contingent 1401 to determine which microneedle structures/reservoirs of the actuator contingent 1402 are to be selected for drug-analyte release, and based on a calculated dose to be delivered, how long a drug release control signal is to be generated at the polymer barrier to cause the polymer barrier to be permeable for release of the drug-analyte, such that the amount of drug-analyte released from the collective microneedle structures of the actuator contingent 1402 is equivalent to the calculated dose of the drug-analyte by the data processing unit. The control signal can be sent via electrical interconnect 1429 coupled to the polymer barrier 1423, such that the open-porosity state of the polymer barrier 1423 allows the drug-analyte to exit the microneedle through the hollow interior 1427 out through the opening of the microneedle structure 1420 and into the biofluid.

For example, based on the drug release control signal received at the actuator contingent 1402 (e.g., via signal processing circuitry) from the processing unit, the release of the drug-analyte from can be controlled (e.g., using multiplexing) to produce the targeted therapeutic dose based on the number and timing of the individually-addressable polymer barriers that are actuated in a manner that can control the size of the porosity (e.g., and thereby the flow), as well as the duration of their open-porous state, controlling concentration of each of the released drug.

EXAMPLES

In some embodiments in accordance with the present technology (example A1), a microneedle sensor device for continuous and minimally invasive electrochemical monitoring of a biomarker in a patient's blood or other physiologically-relevant fluids includes two or more microneedle electrodes operable to detect a parameter associated with the biomarker using two or more different electrochemical detection techniques.

Example A2 includes the microneedle sensor device of any of examples A1-A6, wherein the biomarker is levodopa (L-Dopa).

Example A3 includes the microneedle sensor device of any of examples A1-A6, wherein the one or more microneedle electrodes includes microneedle structure having a hollow portion.

Example A4 includes the microneedle sensor device of any of examples A1-A6, wherein at least one of the one or more microneedle electrodes is configured to detect the parameter by square-wave voltammetry.

Example A5 includes the microneedle sensor device of any of examples A1-A6, wherein at least one of the one or more microneedle electrodes is configured to detect the parameter by chronoamperometry.

Example A6 includes the microneedle sensor device of any of examples A1-A5, wherein at least one of the one or more microneedle electrodes is filled with carbon paste electrode transducer.

In some embodiments in accordance with the present technology (example A7), a continuous analyte monitoring device includes a substrate; and an array of microneedle sensors on the substrate, the microneedle sensors comprising a first working electrode, a second working electrode, and a reference electrode associated with a first microneedle, a second microneedle, and a third microneedle, respectively.

Example A9 includes the device of example A8, wherein each of the first working electrode, the second working electrode and the third working electrode are disposed within a cavity of a respective microneedle structure that protrudes from a surface of the substrate.

Example A10 includes the device of any of examples A8-A9, wherein the first working electrode includes an unmodified electrode, the second working electrode includes an enzyme-modified electrode, and the reference electrode includes a Ag wire.

Example A11 includes the device of example A10, wherein the second working electrode includes an immobilized tyrosinase enzyme able to biocatalyze L-Dopa.

Example A12 includes the device of example A10, wherein the second working electrode includes a permselective protective layer to provide high selectivity and stability of the immobilized enzyme.

Example A13 includes the device of any of examples A8-A12, wherein one or more of the microneedles are hollow.

Example A14 includes the device of any of examples A8-A13, wherein the device is operable for continuous and minimally invasive electrochemical monitoring of a biomarker in a patient's blood or other physiologically-relevant fluids.

Example A15 includes the device of example A14, wherein the biomarker is levodopa (L-Dopa).

Example A16 includes the device of example A14 or A15, wherein at least one of the electrodes detects square-wave voltammetry of the biomarker.

Example A17 includes the device of example A14 or A15, wherein at least one of the electrodes detects chronoamperometry of the biomarker.

In some embodiments in accordance with the present technology (example B1), a sensor device for electrochemical monitoring of an analyte in a biofluid includes a substrate; three or more microneedle structures coupled to the substrate, the three or more microneedle structures each including an exterior wall spanning outward from a base surface of a microneedle structure and forming an apex at a terminus point of the exterior wall, wherein, at a portion of the exterior wall, the microneedle structure has an opening leading in to a hollow region of the microneedle structure that is defined by an interior wall; two or more working electrodes at least partially disposed in the hollow region of at least two of the three or more microneedle structures, the two or more working electrodes including a first working electrode configured to sense the analyte by a first electrochemical detection technique, and a second working electrode configured to sense the analyte by a second electrochemical detection technique different from the first electrochemical detection technique; and at least one counter or reference electrode at least partially disposed in the hollow region of at least a third microneedle structure of the three or more microneedle structures, the at least one counter or reference electrode configured to apply or detect a voltage difference between the at least one counter or reference electrode and at least one of the two or more working electrodes.

Example B2 includes the sensor device of any of examples B1-B26, wherein the sensor device includes a first functionalization material disposed on or integrated with the first working electrode to facilitate an electrochemical reaction involving the analyte and a chemical species of the first functionalization material, wherein the first working electrode is operable to detect an electric signal associated with the electrochemical reaction based on the first electrochemical detection technique applied at the first working electrode.

Example B3 includes the sensor device of any of examples B1-B26, wherein the first functionalization material includes an enzyme to facilitate an enzymatic-based conversion of the analyte at the first working electrode.

Example B4 includes the sensor device of any of examples B1-B26, wherein the first electrochemical detection technique includes amperometry.

Example B5 includes the sensor device of any of examples B1-B26, wherein the second electrochemical detection technique includes non-enzymatic, direct electrochemical detection of the analyte.

Example B6 includes the sensor device of any of examples B1-B26, wherein the second electrochemical detection technique includes voltammetry.

Example B7 includes the sensor device of any of examples B1-B26, comprising a second functionalization material disposed on or integrated with the second working electrode and including a catalyst material to facilitate a redox reaction involving the analyte at the second working electrode, wherein the second working electrode is operable to detect an electric signal associated with the redox reaction based on the second electrochemical detection technique applied at the second working electrode.

Example B8 includes the sensor device of any of examples B1-B26, wherein the catalyst material includes one or both of a graphene film or catalytic metal particles.

Example B9 includes the sensor device of any of examples B1-B26, wherein the two or more working electrodes includes a third working electrode configured to sense the analyte by a third electrochemical detection technique.

Example B10 includes the sensor device of any of examples B1-B26, wherein the third electrochemical detection technique includes amperometry or voltammetry.

Example B11 includes the sensor device of any of examples B1-B26, comprising a third functionalization material disposed on or integrated with the third working electrode, the third functionalization material including an antibody corresponding to the analyte, such that the third working electrode is configured to facilitate an immunoassay reaction involving the analyte and the antibody of the third functionalization material, wherein the third working electrode is operable to detect an electric signal associated with the antibody-antigen reaction based on the third electrochemical detection technique applied at the third working electrode.

Example B12 includes the sensor device of any of examples B1-B26, wherein the antibody is attached to the third working electrode via a self-assembled monolayer (SAM).

Example B13 includes the sensor device of any of examples B1-B26, comprising a third functionalization material disposed on or integrated with the third working electrode, the third functionalization material including an aptamer having an initial conformation tailored to the analyte, such that the third working electrode is configured to facilitate a conformational change when bound to the analyte, wherein the third working electrode is operable to detect an electric signal associated with the conformational change based on the third electrochemical detection technique applied at the third working electrode.

Example B14 includes the sensor device of any of examples B1-B26, wherein the aptamer is attached to the third working electrode via a self-assembled monolayer (SAM).

Example B15 includes the sensor device of any of examples B1-B26, wherein the two or more working electrodes includes a fourth working electrode configured to sense the analyte by a fourth electrochemical detection technique.

Example B16 includes the sensor device of any of examples B1-B26, comprising a fourth functionalization material disposed on or integrated with the fourth working electrode, the fourth functionalization material including an antibody corresponding to the analyte, such that the fourth working electrode is configured to facilitate an immunoassay reaction involving the analyte and the antibody of the fourth functionalization material, wherein the fourth working electrode is operable to detect an electric signal associated with the antibody-antigen reaction based on the fourth electrochemical detection technique applied at the fourth working electrode.

Example B17 includes the sensor device of any of examples B1-B26, wherein the antibody is attached to the fourth working electrode via a self-assembled monolayer (SAM).

Example B18 includes the sensor device of any of examples B1-B26, comprising a fourth functionalization material disposed on or integrated with the fourth working electrode, the fourth functionalization material including an aptamer having an initial conformation tailored to the analyte, such that the fourth working electrode is configured to facilitate a conformational change when bound to the analyte, wherein the fourth working electrode is operable to detect an electric signal associated with the conformational change based on the fourth electrochemical detection technique applied at the fourth working electrode.

Example B19 includes the sensor device of any of examples B1-B26, wherein the aptamer is attached to the fourth working electrode via a self-assembled monolayer (SAM).

Example B20 includes the sensor device of any of examples B1-B26, wherein the three or more microneedle structures include a pyramidal geometry, a conical geometry, or a combination thereof.

Example B21 includes the sensor device of any of examples B1-B26, wherein the two or more working electrodes include carbon paste.

Example B22 includes the sensor device of any of examples B1-B26, wherein the counter or reference electrode includes silver/silver chloride (Ag/AgCl).

Example B23 includes the sensor device of any of examples B1-B26, wherein the substrate includes one or more of polyethylene terephthalate (PET), polyethylene terephthalate glycol (PETG), polyethylene naphthalate (PEN), or polyimide (PI).

Example B24 includes the sensor device of any of examples B1-B26, wherein the substrate is flexible, bendable and/or stretchable.

Example B25 includes the sensor device of any of examples B1-B26, wherein the analyte is levodopa (L-Dopa), carbidopa (C-Dopa), glucose, or insulin.

Example B26 includes the sensor device of any of examples B1-B26, wherein the first functionalization material includes tyrosinase enzyme immobilized to the first working electrode by an electropolymeric entrapment and configured to biocatalyze the analyte L-Dopa.

In some embodiments in accordance with the present technology (example B27), a closed-loop drug-analyte monitoring and delivery system includes a substrate; a microneedle sensor contingent disposed on the substrate; a microneedle actuator contingent disposed on the substrate; and a data processing device in communication with the microneedle sensor contingent and the microneedle actuator contingent, wherein the system is configured to controllably release a drug contained by the microneedle actuator contingent based on a parameter associated with an analyte detected by the microneedle actuator contingent.

Example B28 includes the system of any of examples B27-B35, wherein the microneedle sensor contingent comprises: three or more microneedle structures coupled to the substrate, the three or more microneedle structures each including an exterior wall spanning outward from a base surface of a microneedle structure and forming an apex at a terminus point of the exterior wall, wherein, at a portion of the exterior wall, the microneedle structure has an opening leading in to a hollow region of the microneedle structure that is defined by an interior wall, two or more working electrodes at least partially disposed in the hollow region of at least two of the three or more microneedle structures, the two or more working electrodes including a first working electrode configured to sense the analyte by a first electrochemical detection technique, and a second working electrode configured to sense the analyte by a second electrochemical detection technique different from the first electrochemical detection technique, and at least one counter or reference electrode at least partially disposed in the hollow region of at least a third microneedle structure of the three or more microneedle structures, the at least one counter or reference electrode configured to apply or detect a voltage difference between the at least one counter or reference electrode and at least one of the two or more working electrodes;

Example B29 includes the system of any of examples B27-B35, wherein the microneedle actuator contingent comprises: one or more actuator microneedle structures coupled to the substrate, the one or more actuator microneedle structures each including an exterior wall spanning outward from a base surface of the actuator microneedle structure and forming an apex at a terminus point of the exterior wall, wherein, at a portion of the exterior wall, the actuator microneedle structure has an opening leading in to a hollow region of the microneedle structure that is defined by an interior wall, one or more containment chambers having an interior volume to contain a drug, the one or more containment chambers disposed within a corresponding one or more actuator microneedle structures, wherein a containment chamber includes at least one opening from the interior volume that interfaces with the hollow region of the actuator microneedle structure, and one or more polymer barriers coupled to the corresponding one or more containment chambers at an interface with the hollow region of the actuator microneedle structure, wherein the polymer barrier includes pores of a reversibly tunable porosity.

Example B30 includes the system of any of examples B27-B35, wherein the data processing device comprises a data processing unit including a processor and memory, wherein the data processing unit is configured to, based on the determined parameter, generate a control signal to actuate an expansion of pores of the one or more polymer barriers to an open state or a contraction the pores of the one or more polymer barriers to a closed state.

Example B31 includes the system of example B35, wherein the data processing unit is in communication with the two or more working electrodes and the at least one counter or reference electrode of the microneedle sensor contingent and in communication with the one or more polymer barriers of the microneedle actuator contingent, the data processing unit configured to process electrical signals detected by the microneedle sensor contingent to determine a parameter associated with the detected analyte.

Example B32 includes the system of any of examples B27-B35, wherein the microneedle sensor contingent includes a feature of the sensor device of any of examples A1-A26.

Example B33 includes the system of any of examples B27-B35, wherein the data processing unit is configured to determine a porosity parameter and a time parameter for any selected polymer barriers of the one or more actuator microneedle structures to control a quantity of the drug to be released from the microneedle actuator contingent, wherein the data processing unit generates the control signal based on the determined porosity parameter and the time parameter.

Example B34 includes the system of any of examples B27-B35, wherein the data processing unit is configured to determine a calibration relationship between a present concentration of the analyte from a processed blood sample and the determined parameter of the analyte measured from by the microneedle sensor contingent to determine a time profile for the analyte concentration in blood and in ISF, and wherein the data processing unit is configured to generate the control signal further based on the determined time profile.

Example B35 includes the system of any of examples B27-B34, wherein the analyte and the drug are the same substance.

It is intended that the specification, together with the drawings, be considered exemplary only, where exemplary means an example. As used herein, the singular forms “a”, “an” and “the” are intended to include the plural forms as well, unless the context clearly indicates otherwise. Additionally, the use of “or” is intended to include “and/or”, unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A closed-loop drug-analyte monitoring and delivery system, comprising:
a substrate;
a microneedle sensor contingent configured to detect a plurality of analytes in interstitial fluid (ISF), comprising:
a plurality of microneedle structures coupled to the substrate, each of the microneedle structures including an exterior wall spanning outward from a base surface of a microneedle structure and forming an apex at a terminus point of the exterior wall, wherein, at a portion of the exterior wall, the microneedle structure has an opening leading in to a hollow region of the microneedle structure that is defined by an interior wall,
three or more working electrodes at least partially disposed in the hollow region of at least three of the plurality of microneedle structures, the three or more working electrodes including a first working electrode configured to sense a first analyte by a first electrochemical detection technique, a second working electrode configured to sense the first analyte by a second electrochemical detection technique different from the first electrochemical detection technique, and a third working electrode configured to sense a second analyte different than the first analyte, wherein the first working electrode includes a first functionalization material disposed on or integrated with a surface of the first working electrode to facilitate an electrochemical reaction involving the analyte and a chemical species of the first functionalization material, and
at least one counter or reference electrode at least partially disposed in the hollow region of at least a third microneedle structure of the three or more microneedle structures, the at least one counter or reference electrode configured to apply or measure a voltage difference between the at least one counter or reference electrode and at least one of the two or more working electrodes,
wherein the first analyte includes levodopa (L-Dopa) and the second analyte includes carbidopa (C-Dopa), wherein the three or more working electrodes are configured to concurrently sense the first analyte L-Dopa and the second analyte C-Dopa, wherein the first electrochemical detection technique to sense the first analyte L-Dopa includes chronoamperometry, wherein the second electrochemical detection technique to sense the first analyte L-Dopa includes square-wave voltammetry (SWV), and wherein the third working electrode is configured to sense the second analyte C-Dopa by SWV, and wherein the SWV is operable to concurrently detect L-Dopa and C-Dopa based on their different peak potentials, and
wherein the first functionalization material includes tyrosinase enzyme immobilized to the first working electrode by a permselective anti-interference film and configured to biocatalyze the first analyte L-Dopa;
a microneedle actuator contingent, comprising:
one or more actuator microneedle structures coupled to the substrate, the one or more actuator microneedle structures each including an exterior wall spanning outward from a base surface of the actuator microneedle structure and forming an apex at a terminus point of the exterior wall, wherein, at a portion of the exterior wall, the actuator microneedle structure has an opening leading in to a hollow region of the microneedle structure that is defined by an interior wall,
one or more containment chambers having an interior volume to contain a drug, the one or more containment chambers disposed within a corresponding one or more actuator microneedle structures, wherein a containment chamber includes at least one opening from the interior volume that interfaces with the hollow region of the actuator microneedle structure, and
one or more polymer barriers coupled to the corresponding one or more containment chambers at an interface with the hollow region of the actuator microneedle structure, wherein the polymer barrier includes pores of a reversibly tunable porosity; and
a data processing unit including a processor and memory and in communication with the two or more working electrodes and the at least one counter or reference electrode of the microneedle sensor contingent and in communication with the one or more polymer barriers of the microneedle actuator contingent, the data processing unit configured to process electrical signals detected by the microneedle sensor contingent to determine a parameter associated with the detected analyte, and the data processing unit is further configured to, based on the determined parameter, generate a control signal to actuate an expansion of pores of the one or more polymer barriers to an open state or a contraction the pores of the one or more polymer barriers to a closed state.

2. The system of claim 1, wherein the data processing unit is further configured to determine a porosity parameter and a time parameter for any selected polymer barriers of the one or more actuator microneedle structures to control a quantity of the drug to be released from the microneedle actuator contingent, wherein the data processing unit generates the control signal based on the determined porosity parameter and the time parameter.

3. The system of claim 2, wherein the data processing unit is further configured to determine a calibration relationship between a present concentration of the analyte from a processed blood sample and the determined parameter of the analyte measured from by the microneedle sensor contingent to determine a time profile for the analyte concentration in blood and in ISF, and wherein the data processing unit is configured to generate the control signal further based on the determined time profile.

4. The system of claim 1, wherein the analyte and the drug are the same substance.

5. The system of claim 1, wherein the chronoamperometry implemented on the first working electrode modified with the first functionalization material is configured to measure a tyrosinase-based biocatalytic change of the L-Dopa in the ISF to dopaquinone, and wherein the SWV implemented on the second working electrode that is not modified with an enzymatic layer is configured to measure a change in current as a function of a voltage sweep.

6. The system of claim 5, wherein the chronoamperometry and the SWV are configured to be implemented simultaneously to provide parallel and differing detection techniques on a single detection platform.

7. The system of claim 1, wherein the permselective anti-interference film includes at least one of Nafion or poly(o-phenylenediamine) (PPD).

8. The system of claim 7, wherein the permselective anti-interference film includes the at least one of the Nafion or the PPD, wherein the Nafion is configured to attract the L-Dopa electrostatically while rejecting anionic electroactive interferences from species in the ISF; and wherein the PPD is configured to provide a controlled pore size, pore density, and film thickness of the permselective anti-interference film to tune transport properties of the L-Dopa while rejecting interfering electroactive constituents in the ISF.

9. The system of claim 1, wherein the one or more containment chambers includes:

a first containment chamber that contains a first drug comprising a levodopa drug and that interfaces to a first actuator microneedle structure, and a second containment chamber that contains a second drug comprising a carbidopa drug and that interfaces to a second actuator microneedle structure, wherein the data processing unit is configured to process electrical signals detected by the microneedle sensor contingent to regulate release of the first drug and the second drug based on the sensed analyte L-Dopa and sensed analyte C-Dopa, respectively.

10. The system of claim 1, further comprising:

a pump fluidically interfaced with the one or more containment chambers of the microneedle actuator contingent and configured to contain a supply volume of the L-Dopa.

11. The system of claim 10, wherein the pump is configured on the substrate.

12. The system of claim 1, wherein one or both of the first working electrode and the second working electrode includes carbon paste (CP).

13. The system of claim 1, wherein one or both of the first working electrode and the second working electrode includes a carbon nanotubes (CNT)-chitosan-glassy carbon electrode (GCE), a CNT-chitosan-screen printed electrode (SPCE), or a CNT-gold nanoparticles-graphite electrode.

14. The system of claim 1, wherein one or both of the first working electrode and the second working electrode includes at least one of single-wall carbon nanotubes (SWCNT), multi-wall carbon nanotubes (MWCNT), polypyrrole, graphite, nickel hydroxide nanoparticles ($Ni(OH)_2$NPs), 3D graphene foam, titanium oxide ($TiO_2$) nanofiber-graphene oxide, or nickel hexacyanoferrate-gold nanoparticles (NiHCF—Au NPs).

15. The system of claim 1, wherein the three or more microneedle structures include a pyramidal geometry, a conical geometry, or a combination thereof.

16. The system of claim 1, wherein the substrate includes one or more of polyethylene terephthalate (PET), polyethylene terephthalate glycol (PETG), polyethylene naphthalate (PEN), or polyimide (PI).

17. The system of claim 1, wherein the substrate is flexible, bendable and/or stretchable.

* * * * *